United States Patent
Rontal et al.

(10) Patent No.: US 10,736,686 B2
(45) Date of Patent: Aug. 11, 2020

(54) SURGICAL DEVICE EMPLOYING A CANTILEVERED BEAM DISSECTOR

(71) Applicants: Michael Rontal, Farmington Hills, MI (US); Richard Harrington, Dexter, MI (US); Charles W. Krapf, Livonia, MI (US); Ryan Klock, Ann Arbor, MI (US)

(72) Inventors: Michael Rontal, Farmington Hills, MI (US); Richard Harrington, Dexter, MI (US); Charles W. Krapf, Livonia, MI (US); Ryan Klock, Ann Arbor, MI (US)

(*) Notice: Subject to any disclaimer, the term of this patent is extended or adjusted under 35 U.S.C. 154(b) by 249 days.

(21) Appl. No.: 15/295,595

(22) Filed: Oct. 17, 2016

(65) Prior Publication Data

US 2017/0128122 A1 May 11, 2017

Related U.S. Application Data

(63) Continuation-in-part of application No. 14/641,791, filed on Mar. 9, 2015, now Pat. No. 9,486,235.

(60) Provisional application No. 62/039,783, filed on Aug. 20, 2014, provisional application No. 61/950,924, filed on Mar. 11, 2014.

(51) Int. Cl.
| | | |
|---|---|---|
| A61B 17/22 | (2006.01) | |
| A61B 18/12 | (2006.01) | |
| A61B 17/14 | (2006.01) | |
| A61B 17/16 | (2006.01) | |
| A61B 17/24 | (2006.01) | |
| A61B 17/32 | (2006.01) | |
| A61B 17/00 | (2006.01) | |
| A61B 18/00 | (2006.01) | |

(52) U.S. Cl.
CPC .......... *A61B 18/1206* (2013.01); *A61B 17/14* (2013.01); *A61B 17/1659* (2013.01); *A61B 17/1688* (2013.01); *A61B 17/2202* (2013.01); *A61B 17/22012* (2013.01); *A61B 17/24* (2013.01); *A61B 17/320068* (2013.01); *A61B 2017/00017* (2013.01); *A61B 2017/00734* (2013.01); *A61B 2017/22015* (2013.01); *A61B 2017/320072* (2013.01); *A61B 2017/320084* (2013.01); *A61B 2017/320098* (2017.08); *A61B 2018/00017* (2013.01); *A61B 2018/0094* (2013.01); *A61B 2018/00136* (2013.01); *A61B 2018/00327* (2013.01); *A61B 2018/00589* (2013.01); *A61B 2018/00595* (2013.01); *A61B 2018/00601* (2013.01); *A61B 2018/00642* (2013.01); *A61B 2018/00732* (2013.01); *A61B 2018/00827* (2013.01); *A61B 2018/00988* (2013.01); *A61B 2018/126* (2013.01); *A61B 2018/1226* (2013.01); *A61B 2018/1253* (2013.01); *A61B 2018/1266* (2013.01); *A61B 2217/005* (2013.01); *A61B 2217/007* (2013.01); *A61B 2218/002* (2013.01); *A61B 2218/007* (2013.01)

(58) Field of Classification Search
CPC ....... A61B 17/320068; A61B 18/1206; A61M 25/0158; B06B 1/0603
See application file for complete search history.

*Primary Examiner* — Julie A Szpira
(74) *Attorney, Agent, or Firm* — John G. Posa; Belzer PC

(57) ABSTRACT

A surgical instrument for treating body tissues through narrow body passages employs an elongated cantilevered beam having a proximal end supported in a rigid block and a narrower distal end extendable through the narrow passages. One or more piezoelectric actuators are fixed to the beam surface and energized from an AC source provided by an electrical excitation system through electrodes interspersed with the piezoelectric actuators to produce oscillatory motion of the beam distal end in multiple modes of movement.

52 Claims, 21 Drawing Sheets

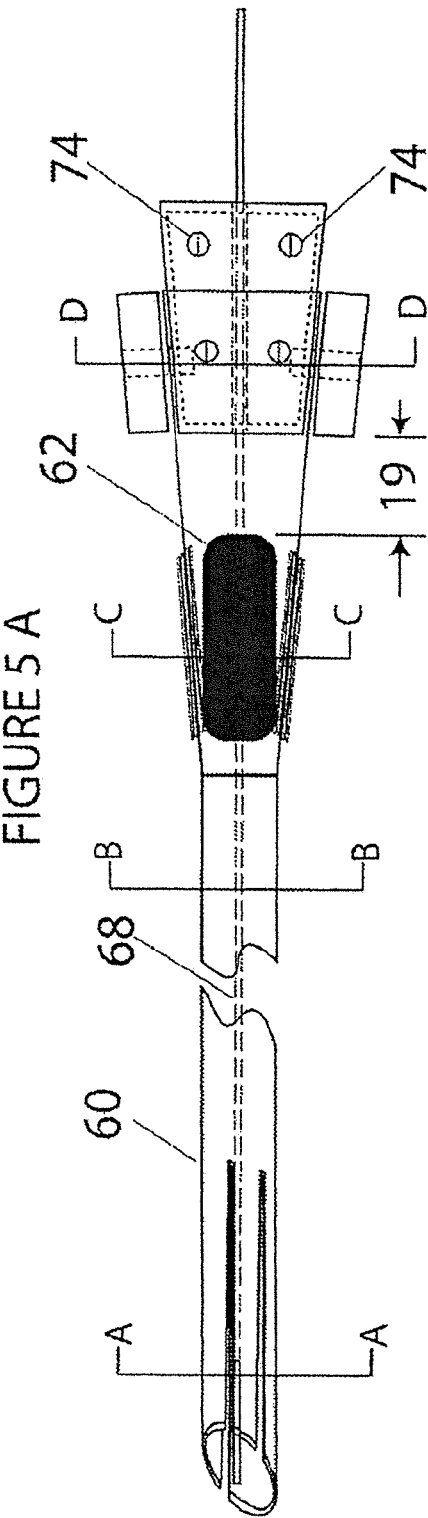
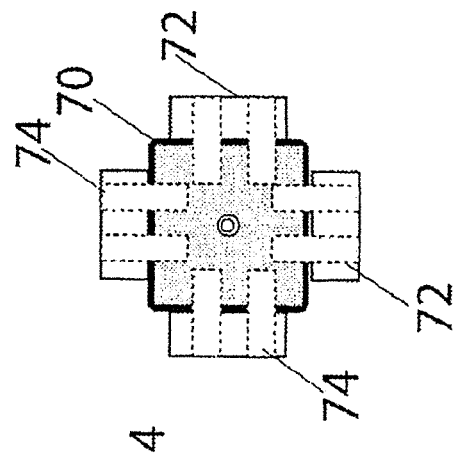
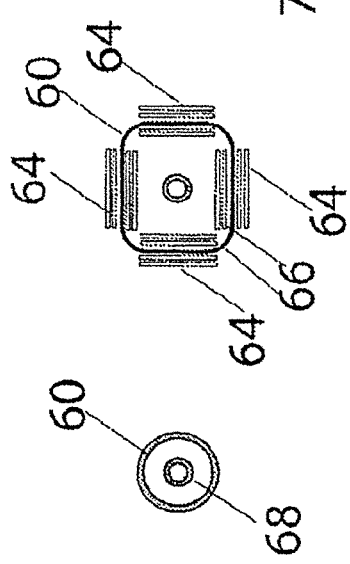
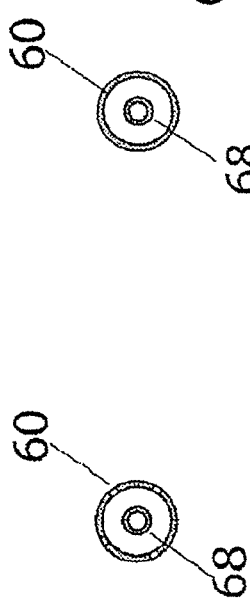
FIGURE 5A
FIGURE 5B
FIGURE 5C
FIGURE 5D
FIGURE 5E

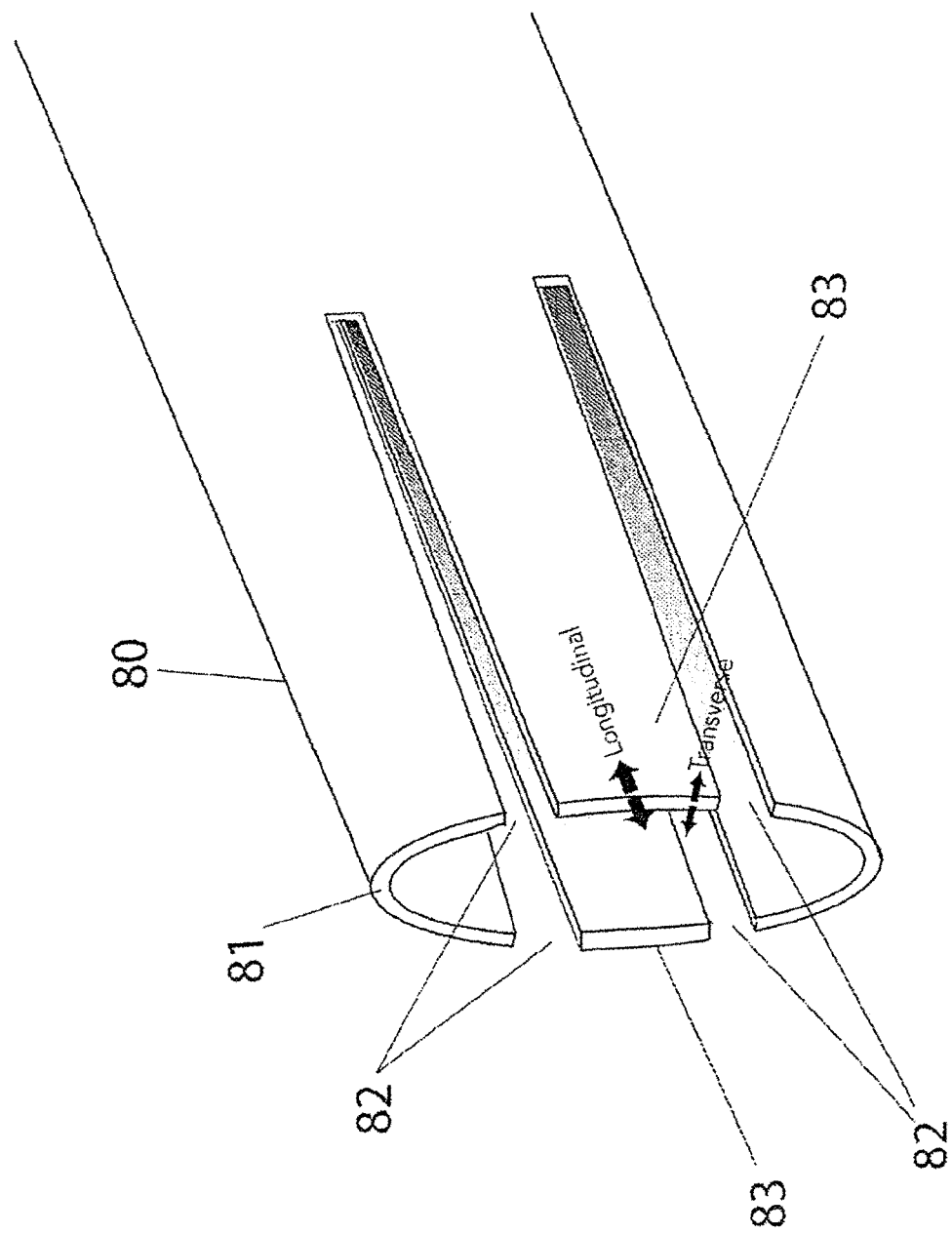

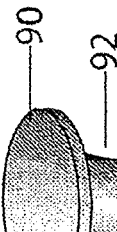
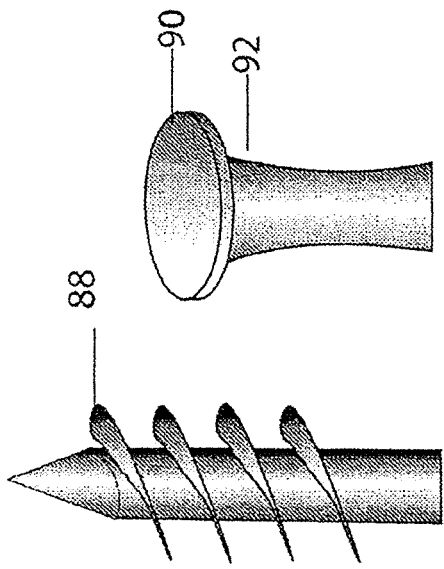
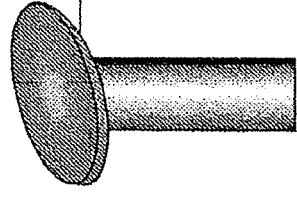
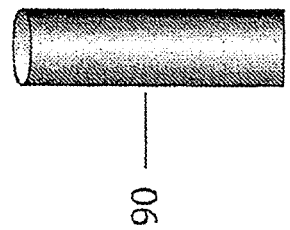
FIGURE 7A  FIGURE 7B  FIGURE 7C  FIGURE 7D  FIGURE 7E
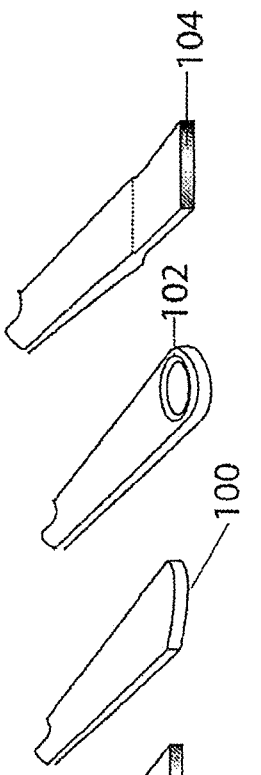
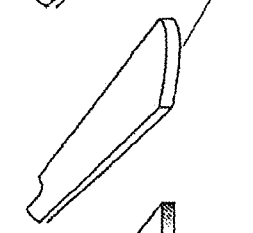
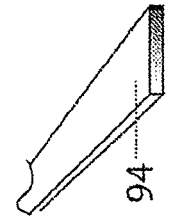
FIGURE 7F  FIGURE 7G  FIGURE 7H  FIGURE 7J  FIGURE 7K  FIGURE 7L

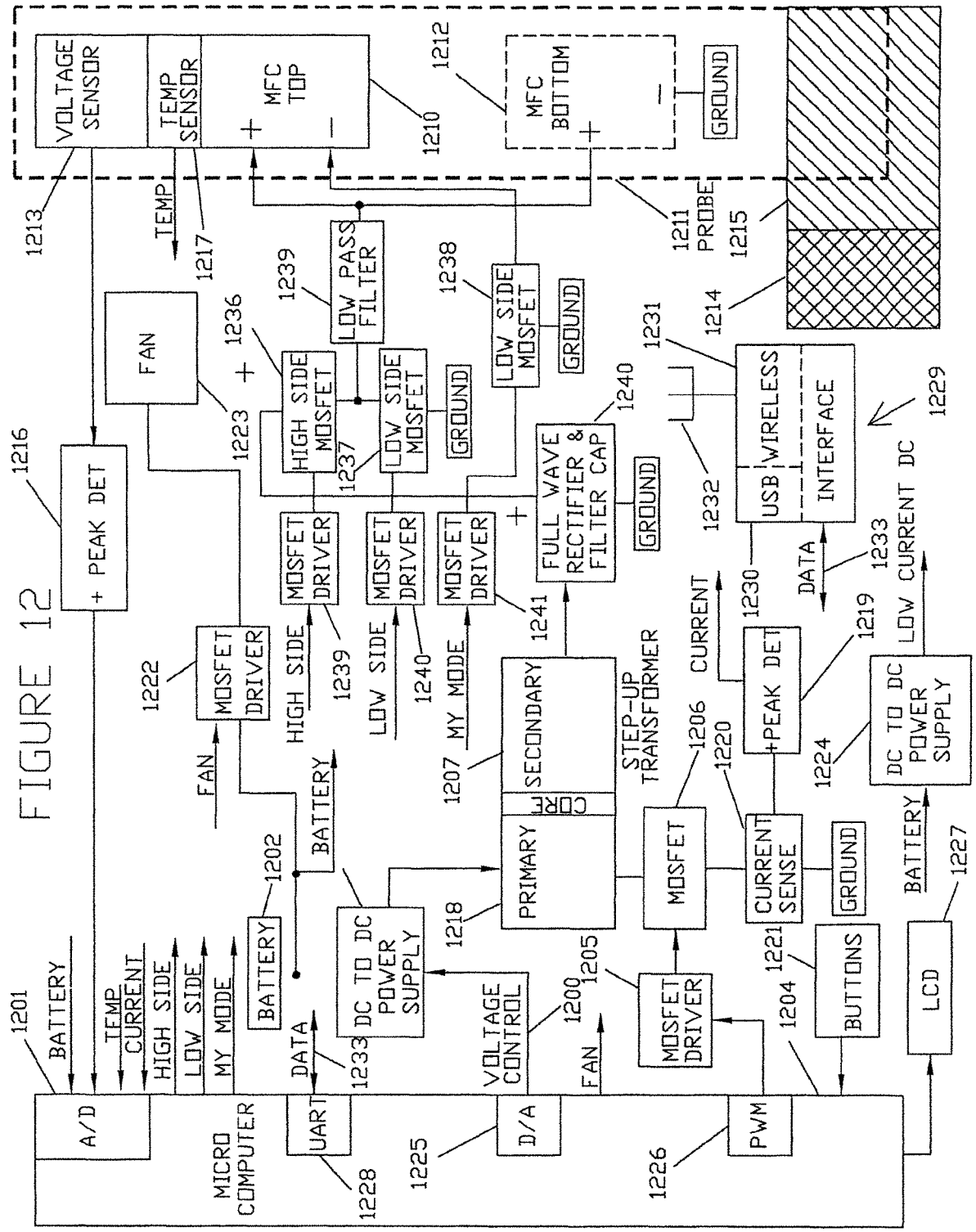

Double bend in probe end to offset

SURGICAL DEVICE EMPLOYING A CANTILEVERED BEAM DISSECTOR

REFERENCE TO RELATED APPLICATIONS

This application is continuation-in-part of U.S. patent application Ser. No. 14/641,791, filed Mar. 9, 2015, which claims priority of U.S. Provisional Application No. 61/950,924 filed Mar. 11, 2014, and U.S. Provisional Application No. 62/039,783 filed Aug. 20, 2014. The entire content of each application is incorporated herein by reference.

FIELD OF THE INVENTION

This invention relates to surgical instruments comprising cantilevered beams driven by macro fiber composites (MFCs) with associated generator, specific tips and case to destroy, dissect, incise, coagulate, and/or otherwise treat tissues through openings and passages to targets within a mammalian body.

BACKGROUND OF THE INVENTION

Surgery is always looking for the most minimal invasion to deep targeted regions. Preformed passageways are always beckoning the surgeon to be used. In one example situation the nasal passages can be used to access diverse regions as skull base, orbit, medial temporal bone, C1 and C2 of the cervical spine, the paranasal sinuses and obviously structures normal to and pathologic in the nasal passages itself. Common to all of these approaches is a long narrow traverse to reach tissues that are often small and adjacent to critical structures such as the eye, brain and spinal cord.

Surgery to this type of region is usually done with one operator working at a time. One hand holds an endoscope for visualization and the other for the operating tool usually one tool for one action and traded out for the next. It is apparent that a fat, rigid, long tool is hard to use under these circumstances to the point of danger. Such is the situation with many of the sonic and ultrasonic devices now available.

For deep and narrow surgery many devices and techniques have been developed and used. For example, cold unpowered steel grasping cutting instrument or a rotating suction debrider such as marketed by Medtronics have been employed. The latter is an improvement as it removes tissue and resulting blood. As procedures are usually done with an endoscope any bleeding rapidly obscures any visualization of the surgical site. To surgically manipulate tissue (disintegrate, incise, elevate and dissect) and not obscure the surgical field with blood, instruments which apply various forms of energy have been developed. These energies include heat, cold (cryosurgery), radio frequency, laser light, plasma and sound. Energy driven surgical tools which apply acoustic energy to tissues can cause tissue effects deep in the body structures through relatively long, narrow passages. Each of these by itself has advantages and faults.

Ultrasonic devices on the market today are based on the "Langevin design" in which an in-line stack of piezo ceramic wafers are compressed between a proximal metal mass (blocking mass) and a metal condenser using a large bolt. The expansion and contraction of the piezo wafers is caused by large potentials across the ceramic wafers. The energy produced by the stack is blocked from proximal extension with a large mass and is received and condensed by the condenser at the distal end of the stack. Various waveguides are then attached to the condenser. Through these the energy thus flows from piezos to distal end. To achieve the best concentration of this sound energy the condenser and waveguide have to be of a length that achieves resonance. The greatest movement then is found at the antinode of the resonant action. The phakoemulsifier as described by Kelman is an example.

The CUSA (cavitron ultrasonic surgical aspirator) is used in brain surgery. Using the same Langevin design, a larger energy source and waveguide associated with a relatively thick walled suction tube is used for neurosurgical removal of brain tumors. The effects are on high water content brain tissue that is repeatedly crushed but not the collagen rich vascular walls. The crushing action produces tiny plugs of crushed tissue that is removed by an integrated suction. Thus disintegrating the tumor and removing the detritus.

Another surgical tool that uses ultrasound is a harmonic scalpel. A rapid longitudinal, reciprocating movement imparted into one jaw of a grasping instrument results in crushing, heating and coagulative destruction that cuts tissue and seals blood vessels. The associated heat generated causes coagulation. The cutting is very precise due to the high rate of movement and the narrow loss of cells in the kerf.

Other surgical instruments employ tissue welding and coagulation produced by sound energy reduced to heat as a waveguide transmits sonic energy to tissues. Blood vessels can be fused closed or various clips can be fused to clamp vessels.

In the early 1990s trials of the CUSA for intranasal surgery (polypectomy) were conducted. This tool was excellent at removing tissue almost bloodlessly but was exceedingly slow. Trial use of CUSA for tonsillectomy has also been published. The advantages were precise intracapsular excisions with little bleeding.

The SonoPet, based on the Langevin design, was introduced recently for otolaryngology work. In one embodiment it is a rigid straight hollow waveguide that suctions blood and detritus. It also is marketed with a variety of rasp tips for vibratory motion and bone abrading. From a nasal surgery standpoint, it can remove a polyp and abrade bone to traverse the skull base or for rhinoplasty.

A device developed in Russia and found in eastern European clinics called a Tonsillor is another high-energy Langevin type ultrasonic device. It is very powerful and is reported to work primarily through cavitation. It is proximately bulky and has a long, relatively thick, rigid waveguide with a variety of tips. It is used near the external surface and straight into the nasal passage as it is too large for precise intranasal work deep in the nose.

SUMMARY OF THE INVENTION

It is the purpose of the present invention to provide surgical instruments that allow surgery in deep recesses through narrow passages such as the nasal passages and associated paranasal sinuses. For the purposes of this disclosure we will often cite surgery of the nose and paranasal sinuses. Those familiar with the art will understand that this device and the many methods of surgical technique can be applied elsewhere. This device uses a narrow and flat beam as a waveguide that is thin, at times curved, at times reinforced, at other times hollow, with a small proximal end energy transducer. It can be made of various metals, alloys and composites. It works using vibratory action so that it provides the advantages of tissue destruction with hemostasis or lack of disruption of small vessels but can also provide a whipping/vibratory action at the beam tip. It is self-correcting for tissue effects on the beam and also can monitor the tissue viscosity for the surgeon to alert encountering bone or passing through tissue into air-containing spaces. This is all made possible by small flat transducers (macro fiber composite pads (MFCs)) and electronics that allow acoustic vibration to do work at the distal end. The electrical source is direct current battery power. A variety of functional tips are described as well as a functional enclosing case.

The devices of the present invention for surgical tissue resection are quite different from previous ultrasound tools. First, the thick, rigid, rod-like waveguides of modern ultrasound tools are substituted with a flat beam, that can at times be modified to accommodate specific purposes, and are made of stainless steel or some other rigid material such as composites. A very important advantage, besides reduced size and weight, is a wider range of resonant-specific lengths. These flat beams offer the precision that comes with isolating the movement in each plane of action. Second, the ultrasonic energy transducer is a Macro Fiber Composite (MFC). An MFC is a piezoelectric device which consists of layers of electrical insulator, interdigitated positive and negative electrodes, piezoelectric ceramic fiber, interdigitated positive and negative electrodes, and electrical insulator in that order, bonded together with a polymer or resin matrix into a patch form-factor.

An electric field applied by the embedded electrodes poles aligns (on a molecular level) the crystals of the piezoelectric ceramic fibers to effect a mechanical elongation and contraction of the fibers. The piezo material can be held together by a flexible resin or in a rigid ceramic matrix. One or more MFCs are bonded to the proximal end of the aforementioned flat beam or embedded within a composite material. Attached to the surface or embedded within the beam, these MFCs transfer their contraction/elongation action to the beam. The result is movement at the distal end. To provide adequate mechanical force to distort the flat beam, multiple MFCs may be aligned or layered upon one another and electrically actuated in unison. Thirdly, the flat beam is cantilevered from a relatively massive blocking mass made of a highly rigid and dense material. This blocking mass serves to prevent proximal movement and to reflect stray sonic and ultrasonic waves toward the distal end of the flat beam. Fourthly, by controlling the phase of actuation of MFCs on either side of the flat beam, two modes of motion may be generated. An extensional motion along the longitudinal axis of the beam (Fz mode) may be generated by actuating MFCs on either side of the flat beam in unison (0 degree phase shift). This Fz mode is characterized by a high-frequency, relatively low displacement motion of the distal tip capable of inducing mechanical displacement of the distal tip in line with the longitudinal axis causing mechanical effects on tissue tissues in contact with the distal tip of the beam. Alternatively, a transverse motion (My mode) may be generated by actuating one MFC or an odd number of MFCs on either side of the flat beam in an opposing fashion (180 degree phase shift). This My mode is characterized by a low-frequency, large-displacement whipping motion of the distal tip capable of minute tearing of animal tissue and blood clot, as well as controlled spreading the Fz actions over a wider area. Rapid transition between the Fz and My modes results in excellent tissue destruction and local hemostasis at the distal tip of the flat beam with precision control.

The system includes a generator operative to produce simultaneous waveforms of varying frequencies, including triangle and square waves at different frequencies. Both waves are in the positive quadrant such that the MFC's receive signals that do not reverse bias the devices which could adversely affect the MFC's. A unique clamping circuit is used to force the high voltage drive signals into the positive quadrant; the negative voltage is equal to one diode voltage drop, or 0.6V. A Half Bridge circuit, used to produce high-voltage square waveforms, uses high voltage MOSFETS and a driver made for driving the gates of the MOSFETS so that only one MOSFET is turned on at one time.

The output of the generator is wired to the MFCs and controlled by the H-bridge circuit to facilitate for very rapid switching between modes of MFC energization where MFC movement is mutually reinforcing, causing axial movement and at other times causing a bending movement of the beam tip. The result is movement of the tip in two planes to do the work of tissue removal. The third plane, x plane, by the geometry of the beam and the nature of vibration moving through the beam has no active movement and achieves the high precision of beam tip tissue interaction/effects by separating each of the other two planes to movement within those planes. As a passive component the x plane can carry extensions that are dragged through engaged tissue lateral to the longitudinal axis of the probe. The MFCs can respond to rapid changes in excitation. The My mode motion can be adjusted to a high frequency which essentially causes tearing and/or churning of the tissue, and the Fz motion can be turned on and off so rapidly as to appear simultaneous and thus cause tissue destruction by both tearing and crushing. The most deflection in the My mode is at the resonate frequency.

The duration for each mode and any delay between switching of modes is entirely controllable. This rapid interplay of these two movements results in excellent tissue destruction under precise control.

As the device uses and controls the interplay between Fz and My movements, the need for a relatively thick, heavy and rigid waveguide is obviated. The relatively narrow distal end can move over a larger area in a controllable fashion. This allows freedom to use any number of designs. The simplest beam cross section is a rectangular flat beam. Those familiar with the art may add changes to this basic flat beam for use in specific situations for example a longitudinal cupping. The beam material may include but is not limited to carbon fiber, stainless steel, titanium, aluminum, layered graphene, and even Pyrex or industrial diamonds. Composites may also be used. The choice is based on the efficiency of transmitting sound energy, the resonant frequency, the length of probe needed, the speed of sound through the beam material, the stiffness of the material, and the need to bend the beam for specific anatomic access.

The efficiency of transmission is important so as not to lose sound energy as the sound travels from proximal end to distal effector end. Stainless steel and titanium are excellent for transmission. In composite materials such as carbon fiber, unidirectional fibers and continuous fibers from proximal to distal tip are important and other attributes to widen the applicability. The composition of material is important for purposes of putting a bend in the material, either curved or sharp. Some embodiments prefer the use of carbon fiber composites which are inexpensive and wherein the speed of sound can be more than twice that of stainless steel or titanium, allowing for ~20 KHz with a probe length of >10 or 15 cm.

The shape of the beam can be wide at the proximal end to accommodate the MFCs and the blocking mass. The beam then rapidly tapers toward the distal end or tip. The more the beam narrows, the higher the energy concentration at the tip.

The shape of the taper varies. In a preferred embodiment the curve is a Bezier. Other curves have advantages as well including a catenary and an exponential or a logarithmic curve, to name a few. A straight taper beam is not as efficient in monolithic metal beams but continuous, unidirectional fibers such as found in carbon fiber beam allow efficient conduction of sound. The distal tip can be thinned or thickened between the two flat sides near the tip. The thickness of the beam is based on the need for stiffness of the beam material for longitudinal motion (Fz motion) or normal movement (My motion).

Other cross-sectional beam shapes are possible. As the flat shape confines the movement to 2 planes where others allow 3 planes and thus more chaotic movement a cupped shape can decrease the movement to only the z or longitudinal axis. Ribs on the side of a rod beam can direct the movement and reduce buckling. Purposeful chaotic movement can also be created with MFCs poled to an angle. Those familiar with the art can introduce cylindrical piezo transducers as well as taking advantage of angled poling, and use of d31 vs d33 effect.

The distal tip can be one of many shapes. For movement in the Fz mode (along the longitudinal axis of the beam), the larger the area of the beam's end, the more negative pressure imparted to the liquid. A flared flat end presents more area to the target tissue. If a flat end is tilted it will enter tissue better. The more surface area in the tissue, the more tissue that is simultaneously removed. Thus, inserting the flared flat end into the tissue produces destruction on both of its sides. Another embodiment would have a series of these tilted, flat and connected surfaces with a sharp tip, essentially creating a screw shape for easy insertion into the tissue and thus causing a long region of tissue disintegration.

As the flat beam has a transverse (My) movement in one direction only, a twist in the beam end can turn the tip 90 degrees and present the tip movement along a different axis. If this edge is sharpened it becomes a knife-edge and makes this My movement applicable to incising. Other shapes are useful. A saw tooth can be used to cut bone, a rasp can abrade bone, and other tips are useful for dissecting through tissue, causing subsurface disintegration, elevating soft tissue off of bone or cartilage, and causing coagulation. Those familiar with the art can devise other shapes or combination of these shapes.

The actual surface of the beam tip is important to ways of increasing efficiency of the tissue effect. Thus, a claw end or a file end can be used for tearing tissue and for abrading bone.

A space between parts of the tip produces useable effects. A simple example is the open slotted end. This can be modified as a closed slot or a circular or hoop shape.

The MFC can be made as a cylinder. MFCs in a cylinder shape or flats set on angle, and even with a spiral piezo composite will produce a twisting action in the beam. Placed appropriately on the proximal end of a cantilevered beam the tip movement can purposely attain movement that is chaotic. Specially designed outer ribs on the rod or conversely slots along the rod can create various patterns of movement.

More advanced beams use multiples of these basic, simple flat beams or can be of a hollow rod shape. Using the walls of a hollow rod or tubular shape is very efficient in carrying sound energy. Hollow MFCs can be attached producing efficient and precise movement with greater movement than possible with a piezo ceramic stack. The end of a tube beam can have multiple slots and thus produce a series of tabs or fingers that act each in its own My plane causing very effective tissue or clot reduction. The effect is to increase the amount of energy brought to the target tissue for faster tissue removal. Also, these arrangements can house suction and irrigation ports as well as a port for an endoscope within the tube, an advantage in freeing a hand of the surgeon.

Of importance is the blocking mass at the proximal end of the beam. This is both the clamp to hold the beam, producing the cantilever and for preventing sound energy from traveling proximately toward the surgeon. The blocker acts as a stationary reference point, adhering to Newton's second law that for every action, there is an equal and opposite reaction. The proximal end of the beam would not move in and out were not for the inertia provided by the blocker and its mass. This mass (inertia) allows the distal end to move in and out by "pushing against" a mass much larger than the probe itself. If the blocker is just 10 times the weight of the probe, a 10% loss will occur (assuming the blocker is rigid). In such a case, the blocker will move in and out at the drive frequency (though its movement will be $\frac{1}{10}$ or the distal probe end movement). In this manner a less massive waveguide requires a less massive blocker.

The block is preferably made of high elastic modulus material (for example steel or tungsten) and due to its inertia, its movement is determined by the ratio of the probe mass extending beyond the blocker and the blocker mass. The waves generated by the MFC at the mechanical resonance of the probe are reflected back to the distal end of the probe by the blocker. This action greatly increases the movement of the distal end of the probe as this repeated reflection has an additive effect. This happens as the blocking mass has a very high density relative to the probe and reflects the sound waves efficiently. The distance between the blocking mass and the MFCs is critical to efficient transfer of as much energy possible in a distal direction. The ideal distance is such that the waves reflected off of the blocking mass are in phase with the waves from the MFCs going towards the distal end of the beam and do not destructively interfere.

One advantage of the MFCs is their rapid response to changes in current flow with relatively large elongation and contraction due to a lack of hysteresis results in high response rates up to about 100 kHz.

MFCs as a unit expand and contract over a larger distance than ceramic piezo discs. This may result in more movement at the distal tip.

Another advantage is the flat configuration and the ductility of the MFC pad. This makes design of the beam easier while still preserving the ability to visualize the target tissue deep in a passage and yet have an ergonomically comfortable tool. An example would be a bend or series of bends in the waveguide producing an offset essentially causing the hand to be out of the visualization path.

The MFCs are preferably attached to the beam with high shear strength epoxies that can withstand the large forces at play. The relation of the pads relative to each other are in a lengthwise or in a lateral orientation. Thus, MFC pads can be applied to the beam side to side with each other or end to end along the longitudinal axis. The proximal end can be lengthened or widened to accommodate more MFCs. MFCs can be cemented on opposing surfaces and interact with other additional MFCs. MFCs can be stacked on each other, though from a practical standpoint a stack of three is the maximum used. The first stacked MFC adds only another 50 percent of the power of the MFC attached to the beam and the second stacked MFC only adds an extra 25 percent. Using these manipulations, a large number of MFCs can be activated in unison for the delivery of a powerful end force.

The simultaneous stimulation of all the MFCs in synchronism will produce substantial longitudinal (axial) reciprocation and power. In contradistinction, if the MFCs are made to actuate in a temporally staggered manner across the beam with the signals to the MFCs on one side producing elongation when the fibers on the opposed side produce contraction, the result is a transverse wave and a subsequent whipping action. This transverse wave may produce a standing wave that approximates the natural frequency of the beam waveguide. This may also be accomplished by simply activating only one MFC for achieving the My movement. The opposing MFC will simply be turned off.

MFCs can also act as sensors. A tiny MFC, or a section of a longer MFC can be attached to the beam can generate signals that vary with the distal end motion. As the beam encounters different tissues with differing viscosities or stiffness, the amplitude of the signals change. This is sensed through a feedback circuit and the drive frequency to the MFCs on the beam can be adjusted. At the same time, the changes in amplitude can be used to alert the surgeon as changes mean encountering differing tissues. The current drawn by the device can also be used to monitor resistance and dampening by the beam due to different densities of the material. In an example situation, with a rapid dampening or a change in the stiffness or viscosity of the tissue may indicate that the beam is nearing bone. Sudden increase in amplitude indicates the beam has exited the tissue and is sitting in air. Detection of either of these events is of importance to the safety of surgery.

A key to this invention is the ability to intermingle two movements at the distal end of the beam. These two movements are produced by the interaction of the MFCs on the proximal end. In its simplest form an MFC is applied on either side of the proximal portion of the flat beam. If the electrical potential is applied at the exact same time to each and they are poled to move in the same direction, an extensional mechanical or sound wave is sent down the beam. This is the Fz movement. If, however, the stimulation of the two sides are out of phase by 180 degrees, one MFC will be lengthening and the other will be contracting. As mentioned before, exciting only one MFC will also cause the beam to bend. Either method will cause a bending of the beam, at the midpoint for example, and is equivalent of a transverse force applied at right angles to the flat side of the beam. This is the My movement.

To make this rapid change the electronic control of the electrical power is key. In one preferred embodiment a half-bridge is used to rapidly switch the excitement of the two MFCs. In this preferred embodiment the electrical signal can be turned on and off very rapidly. Thus, very short bursts of high frequency waveforms to create Fz and then low frequency waveforms to create My movement can be intermingled. The bursts and intervals are so short that it appears as if both are operating at all times. The My is producing a much slower movement that whips the tip to tear or incise the tissue. Yet another advantage of the My movement is to increase the distal end tip area as the My movement may be several mm in deflection. The result is disintegration of the tissue or clean incisions depending on the tip used. For different purposes the amount of time in each mode can be varied. Overall there is a wide range of disintegration or incision or dissection or coagulation or other treatment effects created at the distal end of the beam.

In the brief intervals between these two modes a fast sensor can look for dampening of the tip motion. A feedback to the microprocessor which controls the signal generator can compensate for the dampening. Again the feedback is continuous so seamless monitoring and control is achieved.

The electrical power for this device in one preferred embodiment is a DC voltage provided by a battery, however a medical grade isolation transformer and power supply will also work. This current is controlled by MOSFET's to produce a square wave signal in the primary of a transformer. The voltage is stepped up in the secondary to hundreds of volts. The waveform from the secondary passes through a capacitor and a diode forming a clamping circuit. This clamping circuit forces the waveform to be in the positive quadrant. By this, the square wave or sine wave drives the MFC such that they are forward biased in the Fz and My modes. This is important as the MFCs typically can be driven to +1,500 volts in the forward biased mode, but only 500 volts in the reversed biased mode.

Important for this device is the low voltage (battery) source for the transformer. Besides making the device more transportable it is safer than a conventional wall source and obviates concerns of a ground fault and possible electrocution of the patient or surgeon.

In an alternative embodiment, if an MFC on only one side of the beam is stimulated, the MFC will be lengthening or contracting while the other does not change. This will cause a bending of the beam resulting in the transverse movement of the distal end of the beam as well. My movement is enabled.

The signal generator which generates signals for powering the MFCs is controlled by a microcomputer which outputs a digital mode signal configured to indicate a Fz or My mode and a PWM wave signal used for generating the square waves or sinewave signals.

The electronic control of the electrical power for My mode is achieved in one preferred embodiment, by using a transistor switch controlled by a logic inverter. The logic inverter in controlled by the rapid change of the digital mode output from the microcomputer, turning on and off the transistor switch connected to the MFC on one side of the beam, therefore turning on and off the power for the MFC.

The negative clamp connected to the secondary of the transformer may be modified to clamp the signal to a voltage other than ground. This would allow the MFCs to operate with negative voltage.

It may be desirable to produce a true square wave for powering the MFCs in some circumstances. In one preferred embodiment, the secondary winding of the transformer is connected to a Full Wave rectifier and filter capacitor to generate a high DC voltage up to +1000V. This high voltage is connected to a High Side MOSFET and a Low Side MOSFET with both their drains connected to each other and which are turned on in an alternating fashion to generate a true square wave output alternating from the high DC voltage to ground. The square wave output is connected to +terminals of both the MFCs for powering the MFCs.

Dual mode operation is accomplished by having a Low Side MOSFET connected to the MFC on one side of the beam, turning on or off the current through the MFC on one side of the beam, resulting a longitudinal movement when the Low Side MOSFET is on and both the MFCs are powered in phase or a transverse movement when the Low Side MOSFET is off and only one side of the MFCs is powered.

In an alternative embodiment, Low Side MOSFETs and High Side MOSFETs may be replaced with bipolar switches.

BRIEF DESCRIPTION OF THE DRAWINGS

Other objectives, advantages, and applications of the present invention will be made in the following detailed description of preferred embodiments of the invention. The description makes reference to the accompanying drawings in which:

FIG. 5A is a plan, partially broken away, view of a tubular cantilevered beam;

FIG. 5B is a cross section taken along line A-A of FIG. 5A;

FIG. 5C is a cross section taken along line B-B of FIG. 5A;

FIG. 5D is a cross section taken along line C-C of FIG. 5A;

FIG. 5E is a cross section taken along line D-D of FIG. 5A;

FIG. 6 is a detail of the distal end of a hollow beam tip with slotted ends;

FIG. 12 is a block diagram of another alternative embodiment of a computer controlled system for generating AC driving waves for the MFCs employed with the present invention and for detecting the beam's tip displacement for feedback purposes to control the generated signals;

DETAILED DESCRIPTION OF THE INVENTION

The present invention broadly employs a cantilevered beam, relatively rigidly supported at the proximal end and free to oscillate at the distal end, supporting MFCs on its surface which are electrically powered to induce a variety of motions of the distal end of the beam. A first preferred embodiment of the beam is illustrated in FIGS. 1A-1D.

The beam itself, indicated at 10 in FIGS. 1A-1D, is formed as a thin, generally flat beam formed of a sheet material, monolithics such as stainless steel, but which could include other materials, in particular metals, which are relatively rigid such as titanium, aluminum, or materials such as graphene, Pyrex glass, or industrial diamonds, as well as composite material for example carbon fiber or fiberglass. The beam 10 preferably has a relatively uniform thickness along its length, which in one preferred embodiment was in the range of 0.0040 to 0.0070 inch. Variations in thickness may be advantageous in certain circumstances. Thickness varies with the material used and the action desired.

Figure 1:
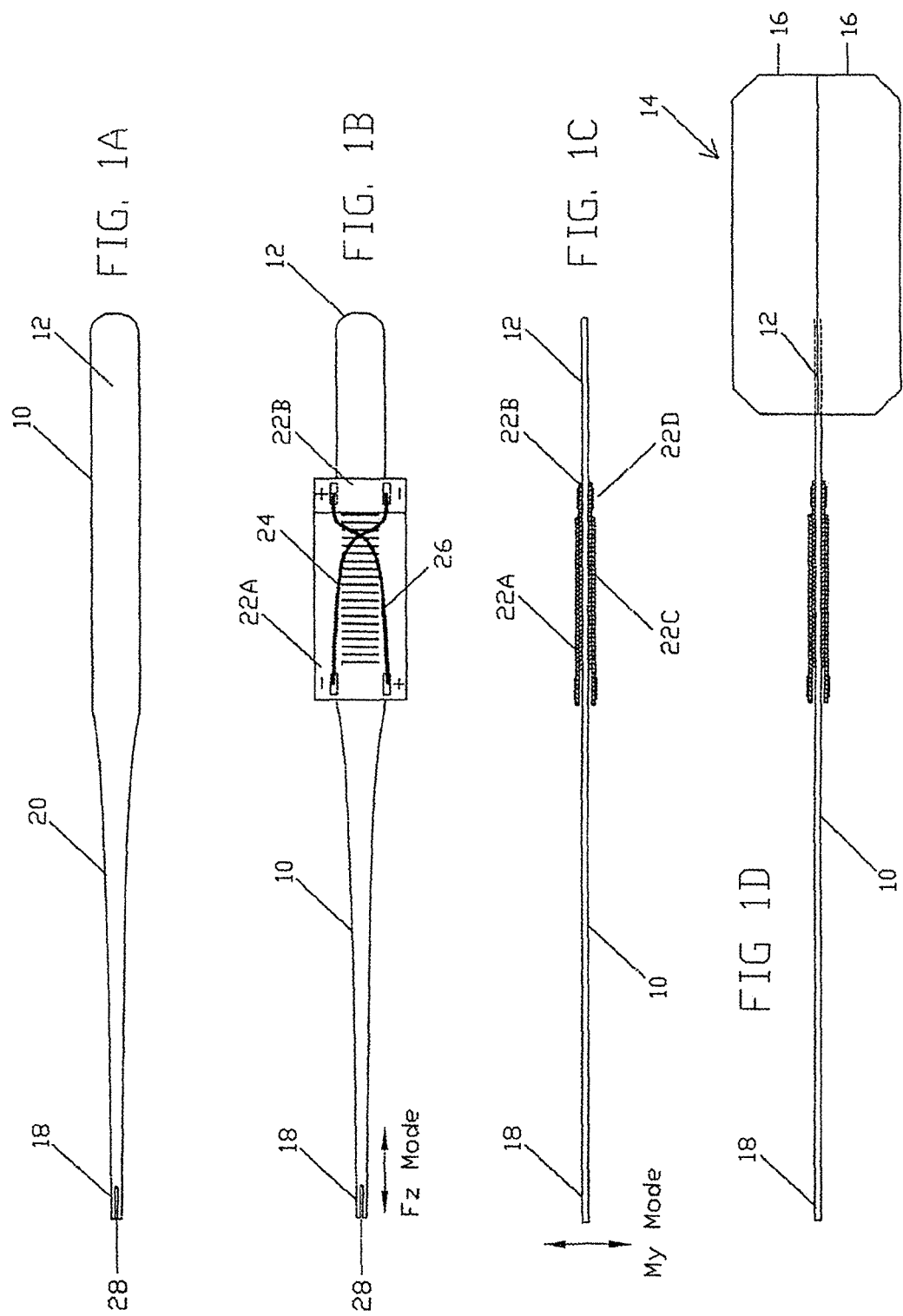
FIG. 1A is a plan view of a cantilevered beam used in a preferred embodiment of the invention and having a slotted tip.
FIG. 1B illustrates the cantilevered beam of FIG. 1A with macro fiber composites (MFCs) adhered to one of its surfaces, with two MFCs connected in parallel.
FIG. 1C is a side view of the cantilevered beam of FIG. 1B.
FIG. 1D is a side view of a cantilevered beam, like FIG. 1C, with its distal end embedded in a sound blocking clamp.

The relatively wide end of the beam, referred to as the proximal end 12, is relatively rigidly supported in a blocking mass generally indicated at 14 in FIG. 1D and consisting of a pair of metal blocks or other material of suitable mass and modulus 16 which have mating flat surfaces that clamp or are cemented to the proximal end 12 of the beam 10. The clamp may be formed of a dense metal, such as tungsten, to better reflect proximal directed vibrations from the MFCs. Other materials are possible and dictated by their mass and/or stiffness and the mass and stiffness of the waveguide. The free end of the beam extending beyond the clamp 14 has a length dependent on the frequency used. The proximal end is wide enough to carry the adhered piezo material and the distal end is wide enough to support active tips or to be specifically machined and narrow enough to concentrate the energy. The relatively wide proximal end of the beam 12 and the distal end of the beam 18 are connected by a curved and tapered section 20. As has been noted, the preferred embodiment of the taper is a Bezier curve. Other curves such as a catenary, an exponential, or a logarithmic curve may be employed as well as a straight taper and a stepped beam al dependent on the beam material and the setting for its use. The beam may be thinned or widened toward the distal end 18. It is possible that the curve on one side may be different than its opposite side.

The MFCs are typically flat and rectangular, and as illustrated in FIGS. 1B-1D may be applied to both flat sides of the beam 10 at a slightly separated distance from the blocking mass 16. As disclosed in FIG. 10, subsequently described in detail, each MFC consists of rectangular rows of piezo crystals embedded in a fibrous composite and shaped into rods. It is possible to ceramic materials too. These are sandwiched between layers of adhesive, electrodes, and a protective film. The electrodes are attached to the film in an interdigitated pattern which transfers the applied voltage directly to and from the ribbon-shaped rods. The MFCs are available from Smart Material Company, Sarasota, Fla., and are described in U.S. Pat. No. 6,629,341, the disclosure of which is incorporated herein by reference. These MFCs may be applied to structures so as to bend or distort the structures, counteract vibrations, or generate vibrations. The materials also act as a very sensitive strain gauge, sensing deformations, noise, and vibration, making them useful for the feedback applications of the present invention. The enclosed piezo sheet may also be a monolithic ceramic poled, for example, along the longitudinal axis like the resin based MFC. Those familiar with the art may substitute other electromechanical modifications.

In order to control the MFCs, a microcomputer will be used. It may be an embedded computer or an external computer. The computer will control the frequency, amplitude and phase of the MFCs and may have a user interface that can contain buttons, potentiometers, and a display (not shown). This computer will also have sensor inputs to monitor the beam while in use. One sensor can be a section of an MFC epoxied on the beam that will generate a voltage proportional to the beam's vibrations. Yet another sensor will be a current sense of the generator power. In practice, the current draw will increase when the beam distal end encounters material such as tissue and bone. The current draw is minimum when the beam is subjected to air.

The MFC or other piezo sensor voltage will be maximum at the beam resonance frequency, and will decrease when the beam is pulled off resonance by encountering tissue or bone. Normally the microcomputer code will change frequency to obtain resonance again, however if it determines that bone has been touched, then it can be programmed to shut down the generator and/or alert the surgeon. There may be cases where bone must be destroyed as well, and this would be a user input to the computer so that it would not shut down the generator, and would optimize the frequency, amplitude, and phasing of the MFCs to achieve the desired result.

The embedded microcomputer can be connected to a PC or other computer such as a tablet. This will provide for data recording, graphing, and sending new code to the embedded microcomputer so that it will be optimized for the particular operation. Time stamping of the data will occur at the embedded micro and will be sent along with the data. Additionally, an endoscope camera (not shown) can be connected to the PC or other computer so that the data from the embedded micro can be time synchronized with the camera data for post processing, statistical analysis, and teaching other doctors, medical students and others in the medical field.

The connection from the embedded micro to the line powered PC will be done so that no common grounds are shared. This is used to prevent ground faults from the line power computer to be transferred to the patient or surgeon. This can be accomplished by wireless transmission, or an optically isolated link such as an OPTO USB connection.

Figure 7:
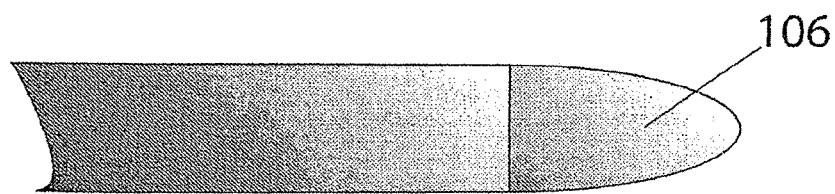
FIGS. 7A-7H and 7J-7T illustrate a range of cantilevered beams having different tips for use in various surgical situations.
Figure 7:
Figure 7:
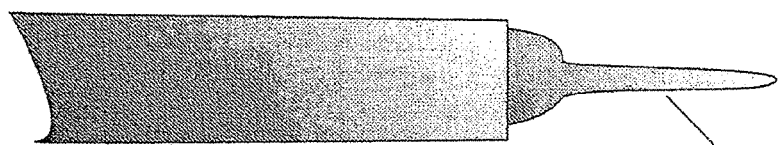
Figure 7:
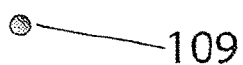
Figure 7:
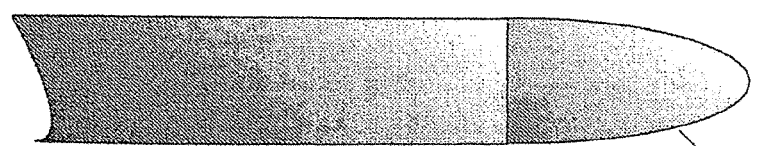
Figure 7:
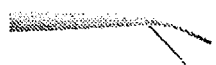
Figure 7:
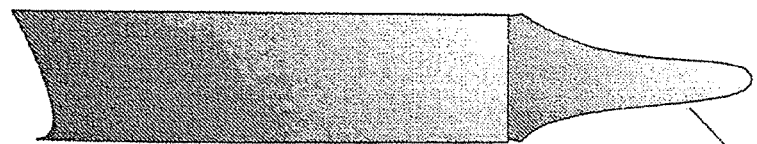
Figure 7:

In FIGS. 1B and 1C two layers of MFCs are applied to each side of the beam 10. MFCs 22a and 22b are applied to the top side, with the units largely overlapping and only the underside units' electrical contacts being exposed. As shown in FIG. 1B, these contacts are preferably connected in parallel by wires 24 and 26. The two bottom layers 22c and 22d are similarly disposed and configured and may be connected in parallel to the upper units 22a and 22b to provide larger deformations. The beam 10 has a slot 28 at its distal tip for purposes of enabling various surgical operations. A variety of other tip designs, some of which are illustrated in FIG. 7, may be employed.

Figure 2:
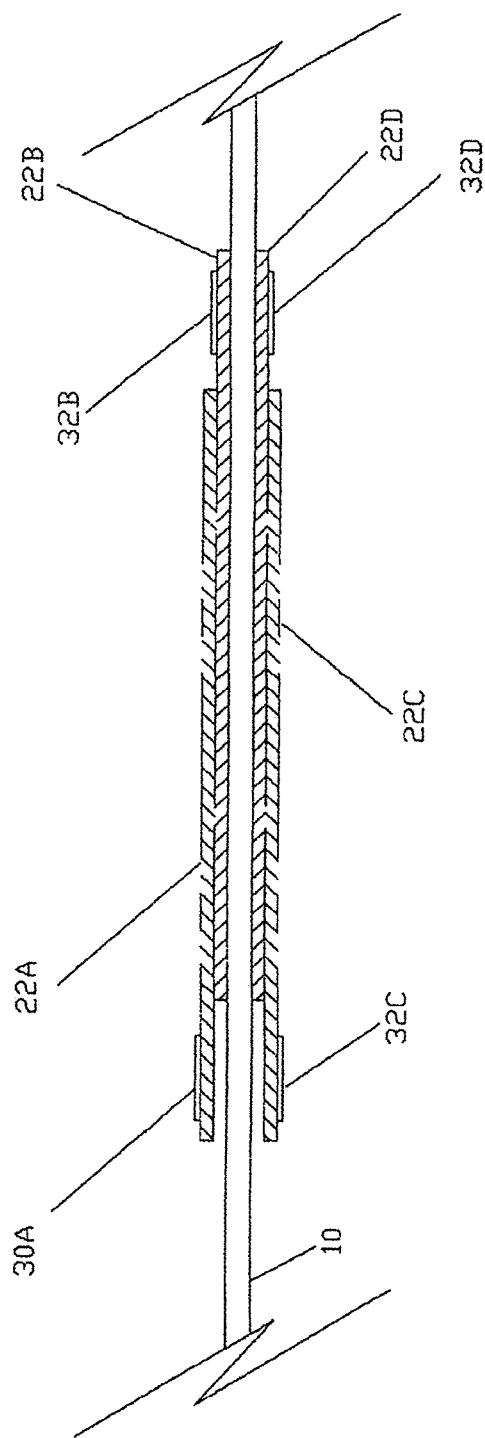
FIG. 2 is an enlarged side view of the section of the cantilevered beam having MFCs applied to its two opposed surfaces.

FIG. 2 is an enlarged side view of the section of the beam 10 incorporating the MFCs. FIG. 2 illustrates the electrical contacts 30a and 30b for the two upper MFCs and 32c and 32d for the lower MFCs. The MFCs are powered by battery powered AC generators illustrated in FIG. 9.

Figure 3:
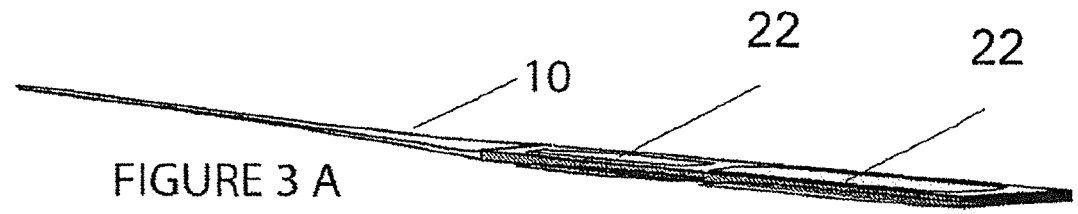
FIG. 3A is a perspective view of the cantilevered beam of FIGS. 1A-1D, having a straight distal end.
FIG. 3B is a perspective view of a cantilevered beam having a downwardly curved distal end.
FIG. 3C is a view of a cantilevered beam having a straight distal end with a proximal end widened to accommodate additional MFCs.
FIG. 3D is a perspective view of a triangular beam supporting multiple MFCs at its proximal end and having a channel that can carry suction, irrigation, and other devices to augment tissue ultrasound interactions.
Figure 3:
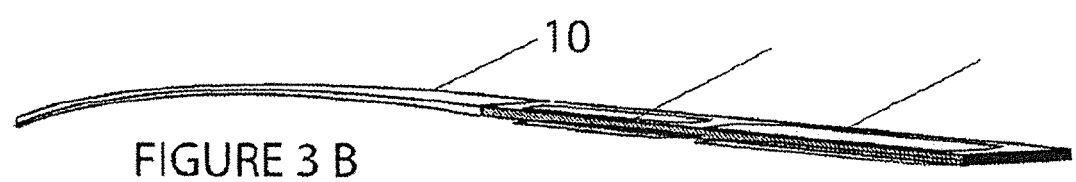
Figure 3:
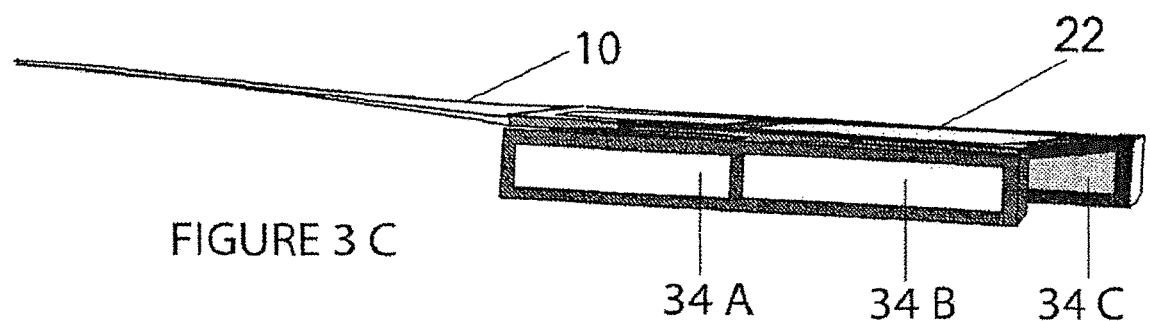
Figure 3:
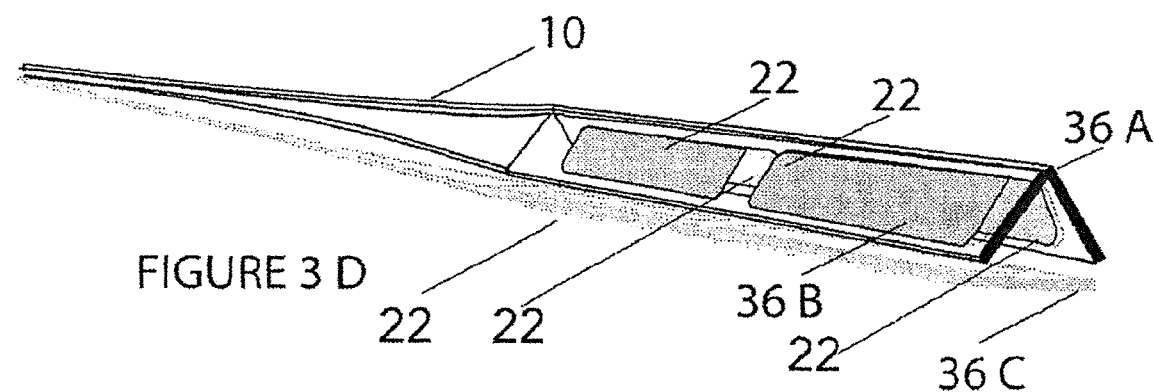

FIGS. 3A, 3B, 3C, and 3D are perspective views of various beam configurations for the cantilevered beams of the present invention showing their supported MFCs 22, but not the blocking masses 14. FIG. 3A illustrates a straight beam, much like illustrated in FIGS. 1A-1D; FIG. 3B illustrates a beam curved along its length; FIG. 3C illustrates a beam having panels which extend normally to the MFC units 22 to support additional MFCs 34a and 34b on one side and 34c on the opposed side. FIG. 3D illustrates a beam having three sections, 36a, 36b, and 36c joined together at their edges in a triangular configuration enclosing a central space that can carry various ports (not shown) for purposes like suction, irrigation, endoscopy, and other surgical purposes. The outer sides of the sections 36a and 36b can carry MFC units 38, which can intensify the motions induced by the MFCs 22. More sides can be added.

Figure 4:
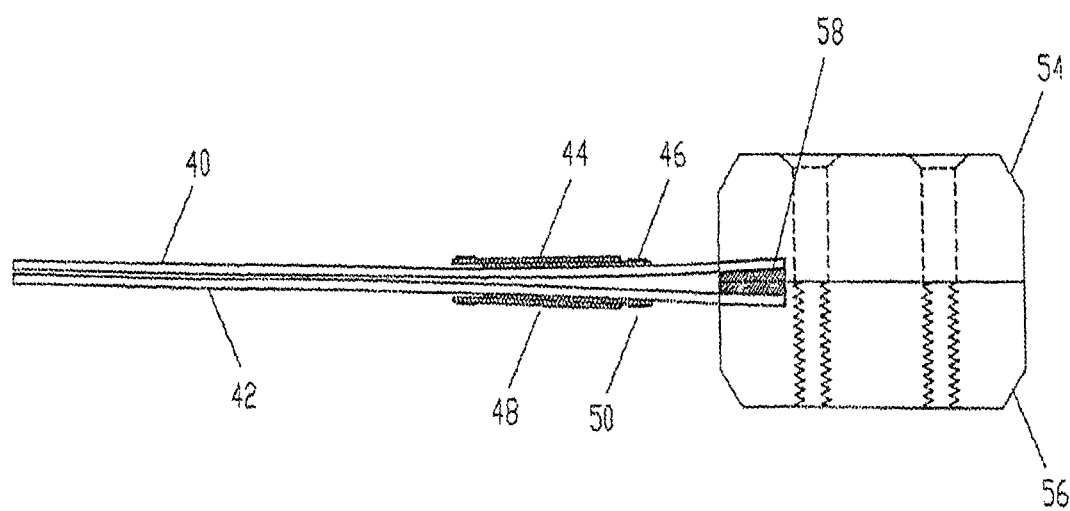
FIG. 4 is a side view of a cantilevered beam employing two parallel beam sections at its distal end and having MFCs adhered to both outer sides of the two beams and having its proximal end anchored in a relatively massive sound blocking clamp.

The dual layer beam 40, 42 illustrated in FIG. 4 has two overlying MFCs 44 and 46 on one of its outer sides and MFCs 48 and 50 on the other outer side. The proximal ends of the beams 40 and 42 are supported in a relatively massive sound blocking clamp 52 comprising a pair of elements 54 and 56 each having flat, mating surfaces. The proximal ends of the two beams 40 and 42 are embedded in an opening in the blocks 54 and 56 and separated by a spacer 58. The blocks 54 and 56 are adapted to accommodate screws or cam clamps or other means of holding the blocker and waveguide together in a permanent or swappable fashion (not shown) which pass through the block 54 and thread in the block 56. Other means of clamping these blocks to the waveguide are possible for design by those familiar with the art.

This configuration can provide strong energy delivery to the distal ends of the beams 40 and 42. The distance from the MFCs to the clamp 52 is preferably an integral number of wavelengths to ensure that the vibrations passing in the proximal direction from the MFCs will be reflected by the clamp, back to the MFCs, so that they reinforce, rather than cancel, the basic vibrations made by the MFCs.

FIG. 5A discloses an embodiment of the invention employing a tubular cantilevered beam generally indicated at 60, in a sense a result of many flat panels. This embodiment has the ability to accommodate a plurality of MFCs 62 which are illustrated in the cross section of FIG. 5D. The separation of the MFCs 64 from the blocking mass 72 is designated 19 in FIG. 5A. A total of eight MFCs are employed with four of them, denoted 64, being spaced about the outer side of the beam and an additional four, denoted 66, are accommodated on the interior of the beam. These can be stacked with a theoretical 24 MFCs acting on the beam. A cylindrical MFC can be used also. This provides a high energy output at the distal end of the beam 60. The interior of the beam can accommodate one or more ports 68 which can carry irrigating fluid and provide suction removal for the destroyed tissue and any irrigating fluid. It could also carry a rigid or flexible fiber optic endoscope for surgical viewing. The tube 60 may gradually converge into a square shape 68 in a proximal direction, so that the proximal end 70, illustrated in cross section in FIG. 5E, is fully rectangular. This rectangular proximal end can accommodate a number of blocking masses 72 on its four sides which increase the overall mass of the proximal end of the tube. Screws 74 join the masses to the proximal end.

In another variation of the invention a tubular beam tip, illustrated in FIG. 6 as 80, may have a number of slots 82 creating "fingers", straight or angled, extending from its distal end to allow for increased whipping action of the distal end and transfer of energy into the tissue to be treated.

The distal tips of the beam may take any of a variety of forms useful to the surgeon to perform particular operations. FIGS. 7A-7T disclose a variety of tip forms.

FIG. 7A shows the distal end of a cantilevered beam 90 having a flat, plain end.

FIG. 7B illustrates a beam end having a flat end expanded laterally at 84 to form a circular end.

FIG. 7C shows a similar flat end 86 which is angled with respect to the central axis of the distal end of the beam. This allows easier entry into tissue so the entire flat plane can be inserted.

FIG. 7D shows a distal end taking the form of a screw 88. Multiple flat plates as in 7C are arranged on the distal end of the rod beam with a sharp screw point to start the end piece into the tissue. Thus all plates may generate cavitation and movement.

FIG. 7E is a distal end with a flat end extended laterally and a concave flare 92 at the immediate distal end adjacent to the end 90.

FIG. 7F shows a plain flat rectangular distal end for the beam.

FIG. 7G illustrates a beam end with a slot parallel to the axis of the beam immediately adjacent the end of the beam, with the slot closed off by the beam.

FIG. 7H is an illustration of a beam end with an open slot 98. The width of the slot can vary as well as the shape of the sides of the slot FIG. 7J is an illustration of a beam end with a rounded edge 100. This can also be a sharp edge.

FIG. 7K is a perspective view of a beam end with a looped slot 102.

FIG. 7L shows a beam with a distal end 104 which is decreased in thickness relative to the proximal balance of the beam.

FIG. 7M is a plan view of a beam end with a dissector tip 106.

FIG. 7N is a side view of the tip 106.

FIG. 7O is a plan view of a beam with a disintegrator tip 108.

FIG. 7P is an end view of the tip 108.

FIG. 7Q is a plan view of a distal tip end 110 which is elevated out of the plane of the balance of the beam as illustrated in FIG. 7R. This tip is useful for elevating soft tissue off of a bony surface.

FIG. 7S is a plan view of a beam with a coagulation tip 112 which has a tapered pointed end 114 as illustrated in FIG. 7T. A small flat end can be used for limited surface coagulation.

Figure 8:
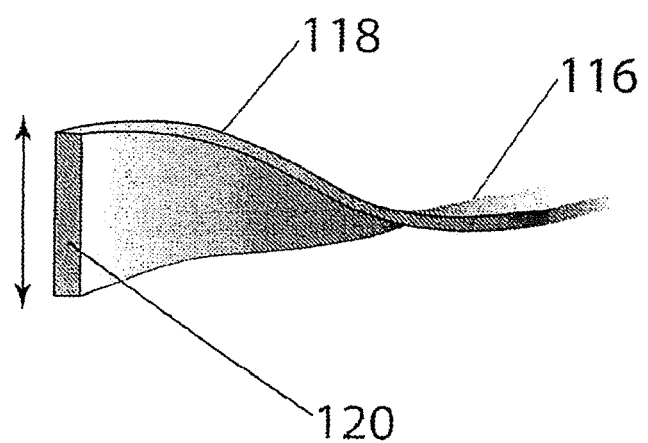
FIG. 8 is a perspective view of the distal end of a cantilevered beam for use with the present invention having a 90 degree twist at its distal end to convert an My movement into a cutting movement.

FIG. 8 illustrates a distal end for a beam 116 with the distal end 118 twisted by 90 degrees out of the plane of the proximal portion of the beam and ending with a sharpened cutting end 120 for cutting soft tissue. This could alternatively be a saw-tooth type end or the like for providing bone cutting motion based on actuation of the MFCs to produce My movement. This end could also end as a rasp for thinning or removing thin layers of bone.

Figure 9:
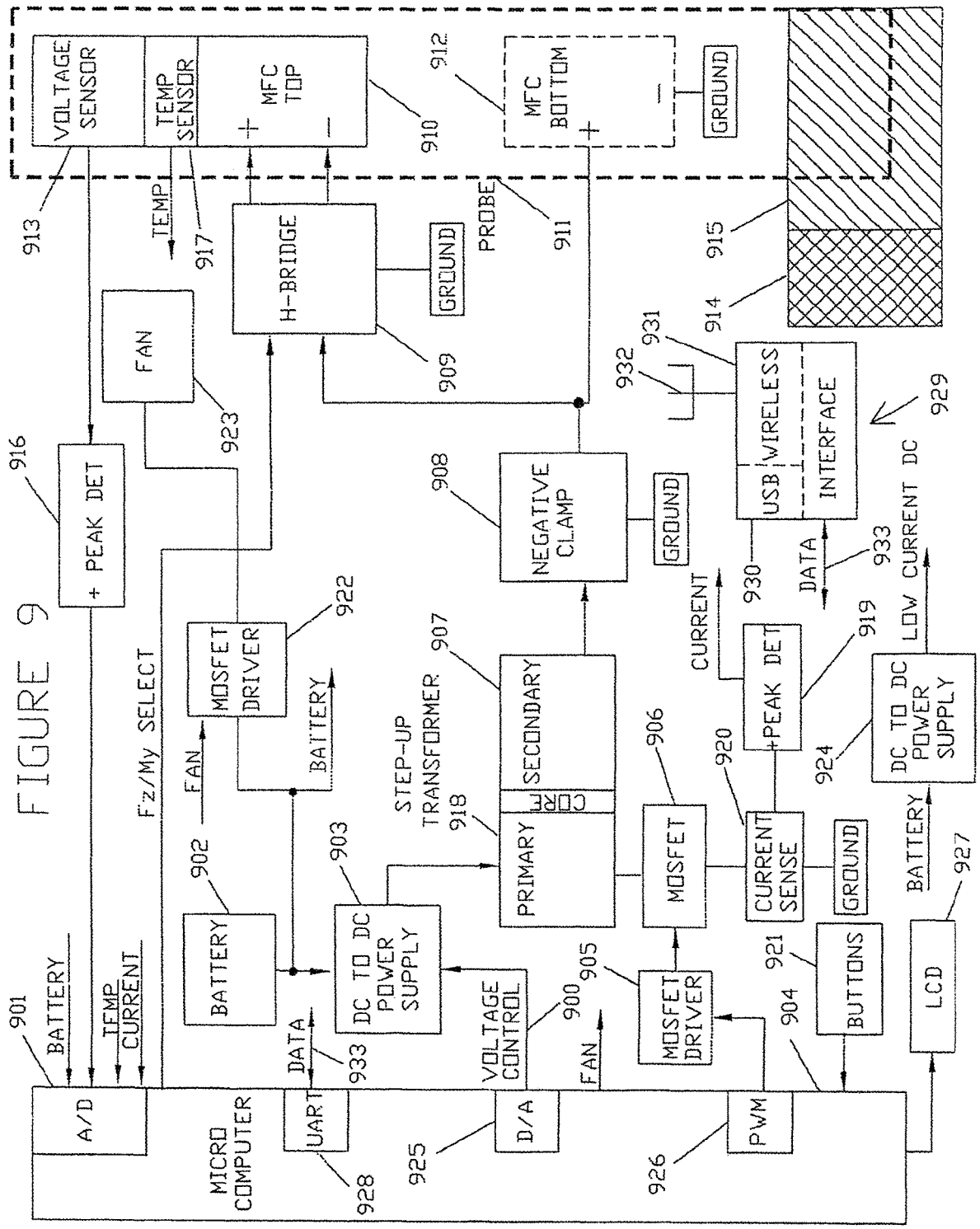
FIG. 9 is a block diagram of a computer controlled system for generating AC driving waves for the MFCs employed with the present invention and for detecting the beam's tip displacement for feedback purposes to control the generated signals.

The control signal generator and feedback circuit for the beam 10 is illustrated in the block diagram of FIG. 9. Broadly, the circuit operates upon a DC supply to generate an alternating current signal approximating a sinewave or triangular wave or saw-tooth wave to power two MFCs disposed on opposite sides of a cantilevered beam, designated the top MFC 910 and the bottom MFC 912 disposed in a beam 911, as illustrated in FIG. 9. The circuit also uses an MFC as a signal generator 913 to detect the deflection of the tip of the beam 911 and feed that signal back through a peak detector 916 to the circuit which generates the AC signal for the two MFCs.

The power for this device is a battery 902 or some other source of DC power that can produce a DC voltage for operation on by microcomputer 904. The microcomputer 904 employs an analog to digital converter 901 which generates a DC voltage control signal on line 900. The signal is provided to a DC to DC power supply 903. The voltage from this power supply is then applied to the primary 918 of a step-up transformer forming part of what is tensed a "sinewave generator" although the signal may be more like a triangular wave or saw-tooth wave. The sinewave generator is composed of the microcomputer 904; the battery 902; the DC to DC power supply 903; the step-up transformer 918, 907; a negative clamp 908; a MOSFET driver 905; a MOSFET 906; and an H-bridge 909.

With the beam tip exposed to free air, the microcomputer programming will maximize the output of a voltage sensor 913 which measures the displacement of the tip of the beam 911. The sensor 913 can be formed by an MFC which produces a voltage when movement is encountered. The positive peak detector 916 produces an AC voltage that corresponds to the peaks of the tip motion sensed by the voltage sensor 913 and produces a voltage proportional to the displacement of the beam tip. Under control of the signal from the peak detector 916, the microcomputer 904 produces a square wave that is connected to the MOSFET driver 905 which increases both the voltage and current to drive a MOSFET gate 906 which has a large capacitance and therefore requires a driver that can supply the necessary current.

The MOSFET 906 has its source connected to ground so that when it is turned on the drain will go close to ground and supply a voltage differential to the primary 918 of the step-up transformer as a result of the other side of the primary winding being connected to the DC to DC power supply 903.

The secondary 907 of the step-up transformer is connected to the negative clamp circuit 908 that keeps the secondary voltage at a positive value. This is desirable because the MFCs can be driven to a positive 1500 volts if they are forward biased and only 500 volts if they are negatively biased. Because the load on the secondary of the transformer 907 is primarily capacitive, like the MFCs, the secondary of the transformer in the capacitive load creates an electrical tank circuit.

When the beam is exposed to tissue it may be pulled off of its resonant frequency in free air and the program of the microprocessor 904 will adjust the frequency of the sinewave generator to maximize the voltage displacement detected by the sensor 913. If, however, a sudden drop of voltage is measured by the A/D 901 from the positive peak detector 916, the program running in the microcomputer will shut down the DC to DC power supply and signal the surgeon that the beam may have contacted a hard substance such as bone. When the beam is in tissue, the output from the sensor is reduced from its voltage in free air.

The power to the beam MFCs is controlled by the microcomputer 904 using a digital to analog converter 925 which provides output on line 900 to the DC to DC power supply 903. The power can be adjusted by the surgeon using up/down buttons 921 providing input to the microcomputer 904.

The beam MFCs can be operated in phase such that the distal end of the beam moves in and out along the central axis of the beam or may be operated out of phase such that the distal end of the beam is forced to move perpendicular to the wide axis of the beam. The phase of the two signals is controlled by the microcomputer 904 through an H-bridge 909. The H-bridge switches the leads of one of the MFCs so it either expands at the same time as the opposite MFC to produce Fz motion or so they expand out of phase producing an My motion so that the MFCs cause a whipping action of the beam tip to occur. The H-bridge 909 is controlled by the Fz/My select signal, an I/O bit of the microcomputer 904.

The current of the sinewave generator is measured by the microcomputer A/D circuit using a current resistor 920 in the grounding circuit of the MOSFET 906. The current envelope signal from the peak detector 916 is measured by the A/D circuit of the microcomputer. This current will change with various beam loading and can be used to optimize the tissue destruction, or cut off power to the beam tip if the program instructs it to do so. The voltage displacement sensor 913 may be an MFC or other piezo device, strain gauge, an electromagnetic device, or any other type of small displacement sensor. If the MFC is used, it produces a voltage using the piezoelectric effect. A +peak detector 916 is used to convert the AC voltage into a +voltage envelope that the A/D can easily convert to a digital value.

The microcomputer 904 controls a MOSFET driver 922 which controls a fan 923 that cools the MFCs 910, 912 and also controls the waste heat from a Peltier junction 914 which cools the blocker 915 which supports the proximal end of the beam 911. The blocker 915 is made of a high modulus of elasticity material so that it reflects rather than absorbs the waves emanating from the MFCs toward the proximal end of the beam 911 back toward the distal end, rather than absorbing those waves. The distance from the end of the blocker to the MFC must be adjusted so that the reflected waves from the blocker are in phase with the MFC waves going toward the distal end of the beam, or energy will be lost.

Figure 10:
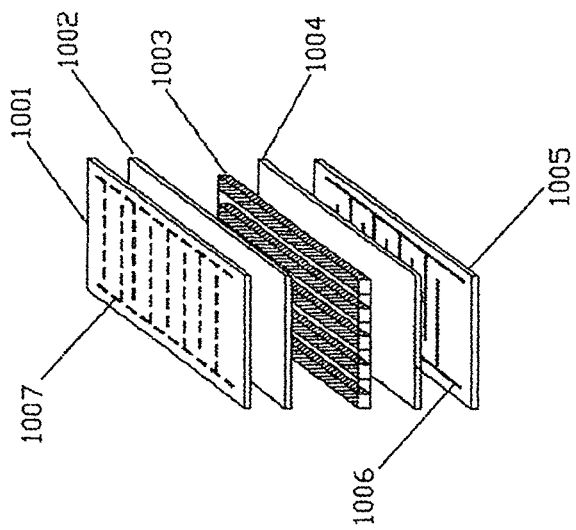
FIG. 10 is a diagram of a preferred version of the MFCs.

A typical macro fiber composite (MFC) useful in the present invention is illustrated in FIG. 10 in exploded form before joining layers into a single composite structure. The top layer 1001 is formed on a rectangular layer of polyimide film and constitutes a pair of electrode structures 1007 consisting of two side electrodes (shown in phantom as they are formed on the underside of 1001), which are connected to the two output terminals of the H-bridge 909. Each of these side electrodes has a group of electrode fingers extending normally to the side electrodes toward the opposite electrodes. These finger electrodes do not contact one another but are intended to bear against the epoxy structure so as to apply their opposite polarity electrical current to the piezo ceramic rods 1003.

The second layer 1002 is a structural epoxy and supports and bonds the other actuator components together.

Layer 1003 is a sheet of aligned rectangular piezo fibers embedded in a fiber composite material. These constitute composite rods with piezo fibers integrated in them. The fourth layer 1004 is another layer of structural epoxy like layer 1002. The fifth layer 1005 is another interdigitated pattern of electrodes like the top layer 1001. When the layers are joined by the epoxy sheets they form a thin surface-conformable sheet in a sealed and durable ready to use package. The electrodes are attached to the film and contact the ribbon-shaped rods of layer 1003 to transfer the applied voltage directly to and from the ribbon-shaped rods. When the assembled unit is affixed to one of the beam beams such as 10, the electrical actuation of the ceramic rods of layer 1003 can cause expansion or contraction of the surface of the beam to which they are attached. It can also act as a generator, sensing motion of the beam tip 18 generating an electrical signal for feedback purposes as has been noted.

Figure 11:
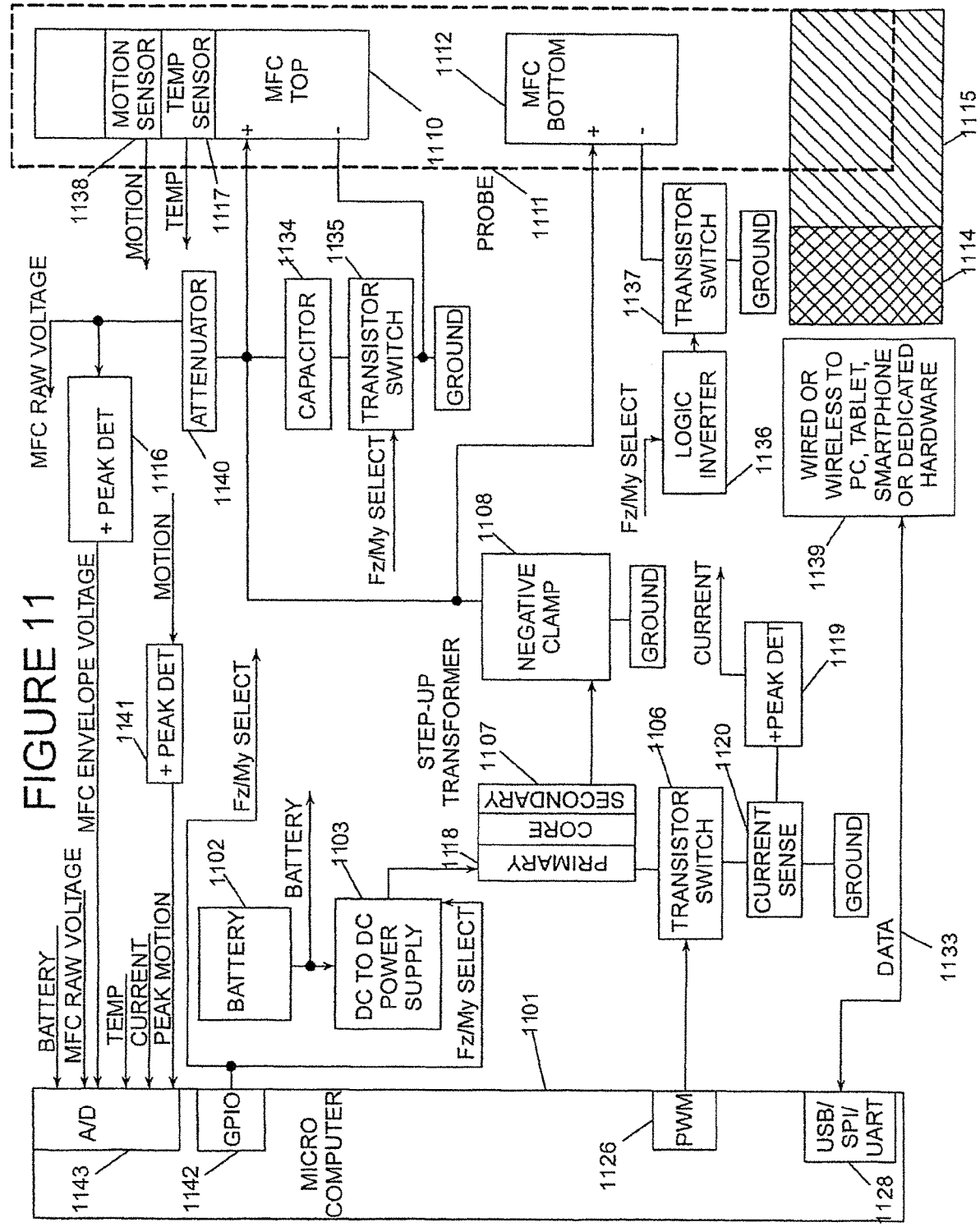
FIG. 11 is a block diagram of an alternative embodiment of a computer controlled system for generating AC driving waves for the MFCs employed with the present invention and for detecting the beam's tip displacement for feedback purposes to control the generated signals.

FIG. 11 shows an alternative embodiment of a control signal generator and feedback circuit for the beam 10. Similar to the control circuit embodied in FIG. 9, a voltage from a DC to DC power supply 1103 is applied to the primary 1118 of a wide-band step-up transformer. When the transistor switch 1106 is turned on, a large current goes through the switch and the voltage at the drain will be close to ground and create a voltage drop across the primary 1118. When the transistor switch 1106 is turned off, the voltage at the drain is higher than ground so the voltage drop across the primary is relative small compared to the voltage drop across the primary when the transistor switch is turned on. The transistor switch 1106 may be implemented as a MOSFET driver and a MOSFET. The MOSFET driver is controlled by a Pulse Width Modulator (PWM) 1126 programmed by the microcomputer 1101 to output a square wave pulses at a frequency of 20 Hz to greater than 20 kHz at a duty cycle of 1% to 99%. As PWM pulses through its highs and lows, the transistor switch is turned on and off changing the voltage drop across the primary, producing sinewave or sawtooth pulses that used to drive the MFCs.

The negative clamp 1108 connected to the secondary 1107 may be modified to clamp the signal to a voltage other than ground. This would allow the MFCs to operate with negative voltage. Typically, MFCs can be operated up to +1500V and down to −500V.

The MFCs may be operated in high frequency Fz mode or in low frequency My mode. The microcomputer 1101 outputs a digital mode signal through a General Purpose I/O (GPIO) 1142. The different modes may require different input DC voltages at the primary 1118. The power supply 1103 senses the mode and changes its output voltage according to the requirements of the mode.

In high frequency Fz mode, the top MFC 1110 and the bottom MFC 1112 are excited in phase to produce longitudinal motion of the distal end of the beam to produce cavitation. In low frequency My mode, only the top MFC is excited to produce a transverse motion at the distal end of the beam. The phase of the two signals is controlled by the microcomputer 1101 through a transistor switch 1137 and a logic inverter 1136. The transistor switch 1137 may be implemented as a MOSFET and A MOSFET driver. In both Fz and My modes, the top MFC is supplied with high voltage pulses from the secondary 1107. The voltage drop across the top MFC keeps the top MFC excited in both modes. When the digital signal output through GPIO 1142 is low, the logic inverter 1136 inverts the digital signal to high and turns on the transistor switch 1137. The drain of the MOSFET goes close to zero volts but produces a voltage drop across the bottom MFC as a result of high voltage pulses supplied to the other end of the bottom MFC, exciting the bottom MFC. When the digital signal output through GPIO 1142 is high, the logic inverter 1136 inverts the digital signal to low and turns off the transistor switch 1137, cutting off the current through the bottom MFC.

A capacitor 1134 is connected to both negative clamp and the MFCs. The capacitor 1134 is switched in and out of the circuit by a transistor switch 1135. Similar to other transistor switches, the transistor switch 1135 may be implemented as a MOSFET and a MOSFET driver. The MOSFET driver is controlled by the same digital mode signal from the microcomputer 1101 and the source of MOSFET is connected to ground. When the digital signal is high (indicating low frequency mode), the transistor switch 1135 is turned on creating a voltage drop across the capacitor 1134 until the capacitor 1134 is fully charged. Along with the secondary 1107 of the transformer, the capacitor 1134 forms a resonant tank at the low frequency mode.

When switching modes, the MFC Raw Voltage is monitored by the microcomputer 1101 and the mode switch is timed so that the voltage across the capacitor 1134 is zero at the time of the switch. This prevents a large inrush of current into the capacitor 1134 and the secondary winding of the transformer at the time of the switch.

The MFC temperature is measured with a temperature sensor 1117 and is monitored by the microcomputer 1101. If the MFC temperature exceeds a predefined safe level, the excitation is shut down. Instead of being shut down by suddenly stopping the PWM signal causing a voltage spike that may damage components of the system, the system may be safely shut down by slowly reducing the PWM duty cycle to 1% and then stopping the PWM signal. By the time the duty cycle is 1%, there is very little energy stored in the system and stopping the PWM signal produces no voltage spike.

A slight modification of the circuit may allow the microcomputer to also monitor the current through the MFCs.

A user interface processor (not shown) is provided with the microcomputer 1101 to perform data logging and may log all measured values such as the MFC Raw Voltage, the MFC Peak Voltage, the MFC temperature, frequency, mode, Peak Motion Sensor Voltage, time, etc. The microcomputer 1101 may also capture the MFC Raw Voltage at high speed and display the waveform at the user interface processor like an oscilloscope.

The User Interface component 1139 may be a PC, Tablet, Smart Phone or dedicated touch screen. The microcomputer 1101 may be hardwired to the User Interface 1139 using a connection such as Universal Serial Bus (USB), or use short distance communication protocols such as Bluetooth.

The microprocessor may perform a frequency sweep and use the feedback from the motion sensor 1138 to plot out a Motion vs. frequency graph on the User Interface. The graph may be used to find various peaks.

If exposing the MFCs to a large electric field (high voltage) at an elevated temperature for a specified length of time, the MFCs may be repoled with a slight modification of the design.

It may be desirable to produce a true square wave in some circumstances. The design illustrated in FIG. 11 has been shown to produce output pulses with a sawtooth waveform, but may be modified to produce output pulses in a true square waveform. FIG. 12 illustrates an embodiment of such design which produces output pulses with a square waveform.

The circuit shown in FIG. 12 has the secondary winding of the transformer 1207 connected to a Full Wave rectifier and filter capacitor 1240 to generate a high DC voltage up to +1000V. This voltage is connected to a High Side MOSFET 1236 that is turned on by a MOSFET driver 1239. A Low Side MOSFET 1237 is turned on by a MOSFET driver 1240 with its drain connected to the drain of the High Side MOSFET 1236. The drains connected together go to +terminals of both the top MFC 1210 and the bottom MFC 1212.

The negative terminal of the top MFC is connected to a Low Side MOSFET 1238 that is turned on by MOSFET driver 1241. The High Side MOSFET 1236 and the Low Side MOSFET 1237 are turned on in an alternating fashion, generating a square wave signal at the drains of the both MOSFETs, therefore supplied to the +terminal of the top MFC. The highs of the square wave signal is pulled up to the voltage of the filter capacitor 1240 when the High Side MOSFET 1236 is turned on and the Low Side MOSFET 1237 is turned off, while the lows of the square wave go to ground when the High Side MOSFET 1236 is turned off and the Low Side MOSFET 1237 is turned on.

The driver for High Side FET and the driver for Low Side FET may be controlled by the PWM signal from the microcomputer 1201 such that when the PWM signal is high, the square wave output to the MFC is high and the square wave output is ground when the PWM signal is low.

In an alternative embodiment, the High Side FET and the Low Side FET may be replaced by high side and low side bipolar switches, in which case the collectors of the two bipolar switches are connected to each other and to the +terminals of the MFCs.

Dual mode operation is accomplished by having the Low Side MOSFET 1238 connected to the—terminal of the top MFC. When the High Side MOSFET is turned on and the square wave signal is at its highs, having the Low Side MOSFET 1238 turned on causes the—terminal of the top MFC to be close to ground, resulting in currents flowing in the same direction in both the MFCs and both MFCs being excited in phase as square wave signal oscillates. If the Low Side MOSFET 1238 is not turned on, there is no current flowing in the top MFC and only the bottom MFC is excited as square wave signal oscillates, resulting in a transverse motion of the distal end of the beam 10. As the Low Side MOSFET 1238 is turned on and off, the beam 10 goes from being excited in phase to have a longitudinal motion to being excited out of phase to have a transverse motion. The frequency of the square wave signal may be adjusted to very high when the Low Side MOSFET 1238 is turned on and to very low if the Low Side MOSFET 1238 is turned off to generate a high frequency Fz mode alternating with a low frequency My mode.

There may be a need to prevent extreme inrush current to the MFCs as the capacitive resistance of the MFCs would be very low because of the very fast rise and fall times of the MOSFETs. A 20 kHz square wave with very fast rise and fall times would produce harmonics in the MHz range of which would cause possible damage and certainly a lot of waste heat at the MFCs. A Low Pass filter 1239 is used to adjust the slew rate of both the High Side FET 1236 and the Low Side FET 1237 to prevent damage and overheating to the MFCs. This filter may be as simple as a resistor or an inductor.

It will be appreciated that instruments and systems constructed in accordance with this invention include various subsystems, some or all of which may be improved or modified to improve performance, reduce size or cost, or optimize other characteristics depending upon the application. Potential optimization may include the design of the probe itself, including material(s), angulation, electromechanical transducer and piezo configurations, blocker device and functional tips. The case and power source/generator of resultant instruments may be modified and improved to optimize heat removal and provide additional functionality such as coagulation.

Probe Considerations

In accordance with this invention, the MFCs may be positioned wherever the probe is wide enough to accommodate them, and where they can optimize the resonance at the desired frequency. The basic shape of this planar waveguide is like a paddle. The proximal end is wider and accommodates both the MFCs and the blocker. Just beyond the MFCs the paddle narrows. The transition from wide to narrow can be one of or a combination of a number of designs. One efficient profile for delivering sound to the tip in a monolithic probe is a stepped shape. This abrupt transition, at a 90° or other abrupt angle, is capable of delivering the most energy but also has the most stress concentration at the transition. This will decrease the life of the probe unless fillets are used. The fillet size is chosen so that the stress level is acceptable, and not so large that it significantly reduces the advantages of the stepped probe.

The main advantage of the stepped probe is its ability to increase the distal end movement compared to a simple beam. The reason for this is conservation of energy—the energy in the wide portion of the probe is transferred to the smaller width of the probe, causing the distal end of the probe to move much more than the section where the MFC's are placed. The MFC's actually expand and relax and or contract the probe material directly under the MFC's. Contraction will occur if the MFC's are driven with a reverse polarity compared to the expansion polarity. Relaxing of the probe will occur if the MFC potential goes to zero volts.

There are many different curves possible for the transition. Wang et al has tested this with metal probes and found the Bezier curve to be most efficient of the curves though it is not all that different from the catenary curve. A straight taper is not efficient at all. With metal probes a tapered probe is not efficient but with a carbon fiber probe with fibers individually carrying the sound energy tapered probes can be effective. Those familiar with the art will see that many other curves or small fillets are possible, for example, catenary or exponential or combinations of these curves.

The thickness of the probe is chosen for its ability to not buckle under the loads induced. Thus, too thin and it buckles, and too thick and it will not move well enough. Too thick and the y movement is reduced stiffness and with an increased mass the frequency in the z plane decreases. A thinner probe is better for producing the whipping action (y plane). How narrow the distal end should be is dictated by the surgical needs and the ability to withstand buckling as the probe engages the target tissue. Modifications added to the flat beam can add to the buckling strength, for example, a cupped shape modifying the flat feature or the addition of ribs. A cup shape further defines movement as it prevents movment in both the x and y plane. Further, the length of the probe is critical to reach the tissue yet encourage control through ergonomics. In our example of the nasal passage, the distance from outer edge of the nostril to the deepest paranasal sinus is on average 9 centimeters.

To augment the power developed by the MFCs, resonance is developed and indeed encouraged within the waveguide. The sine wave that traces the movement of the probe material as sound is put through it is seen to have its apogee and nadir at the ¼ wave and ¾ wave. The tip should be at one of these points to attain maximum movement. The formula for wavelength in a medium is $\lambda=c/f$, where $\lambda$ is the wavelength, c=speed of sound in the material and f=frequency. It is seen that the higher the frequency the shorter the wavelength within the same material. With a higher frequency in a certain length of time more work can be done. It is thus efficient to have a high frequency. However this will lead to shorter wave lengths. The variable that is left to change is the speed of sound and this requires a variety of materials to choose from in design.

Probe Composition

One of the problems with familiar metals such as stainless steel and titanium is that the speed of sound of each is not significantly different. Stainless steel has a speed of about 5900 meters/second and titanium a speed of about 6100 meters/second or less. This produces probes that may not fit a particular use, for example the nasal use described above. Materials with a higher speed are more useful for probes entering the nose. It has been discovered, for example, that carbon fiber may be very useful. The speed of sound is between 11600 m/s and 22000 m/s, depending on the exact composition of the carbon fiber. In addition, this material has a significantly higher modulus of elasticity so that thickness and buckling are less of a problem This is accomplished with a reduction in mass.

Carbon fiber is manufactured as a fabric with unidirectional and multidirectional conduction of sound. Unidirectional is more efficient for this probe as the sound is conducted within the carbon fibers, and advantageously uninterrupted, from source to target. In addition, the carbon fiber conducts heat very efficiently and is advantageous carrying heat from electrical devices when embedded within its substance. In addition to carbon fibers, solid probes of other materials are possible. Industrial diamond and sapphires are possible sound conductors as is beryllium or beryllium copper. When needed a slower material may be used such as brass.

While flat probes can be inexpensively made from sheets of carbon fiber, a particular design for carbon fiber can be made by creating a form or mold. For example, a flat composite of carbon fiber sheets epoxied together or folded into a form or mold. The thin fabric is laid up in the form, layer by layer with each layer epoxied into place.

There are many advantages to this type of material for designing a probe. First, there is no need for machining as is necessary for titanium or stainless steel. Flat sheets of carbon fiber composite can be cut directly. With laying up the unidirectional carbon fiber plies, the sheets may also be folded so that each carbon fiber extends the entire length of the probe and energy within the fiber is carried from one end to the other uninterrupted as opposed to a cut fiber that will deposit its sound energy into the intervening resin with a decrease of energy to be carried to the tip. If all the fibers are parallel and extend from proximal to distal, a rectangular probe can be made with a specialized MFC created to fit this rectangular probe. Likewise individual fibers could be laid down and epoxied in place. Specialized designs are also possible such as reinforcing or reshaping the flat surface if more strength against buckling is needed. Carbon fibers can be created that are larger proximally and narrower distally thus concentrating the energy. Those familiar with the art can expand on this.

Figures 13A, 13B:
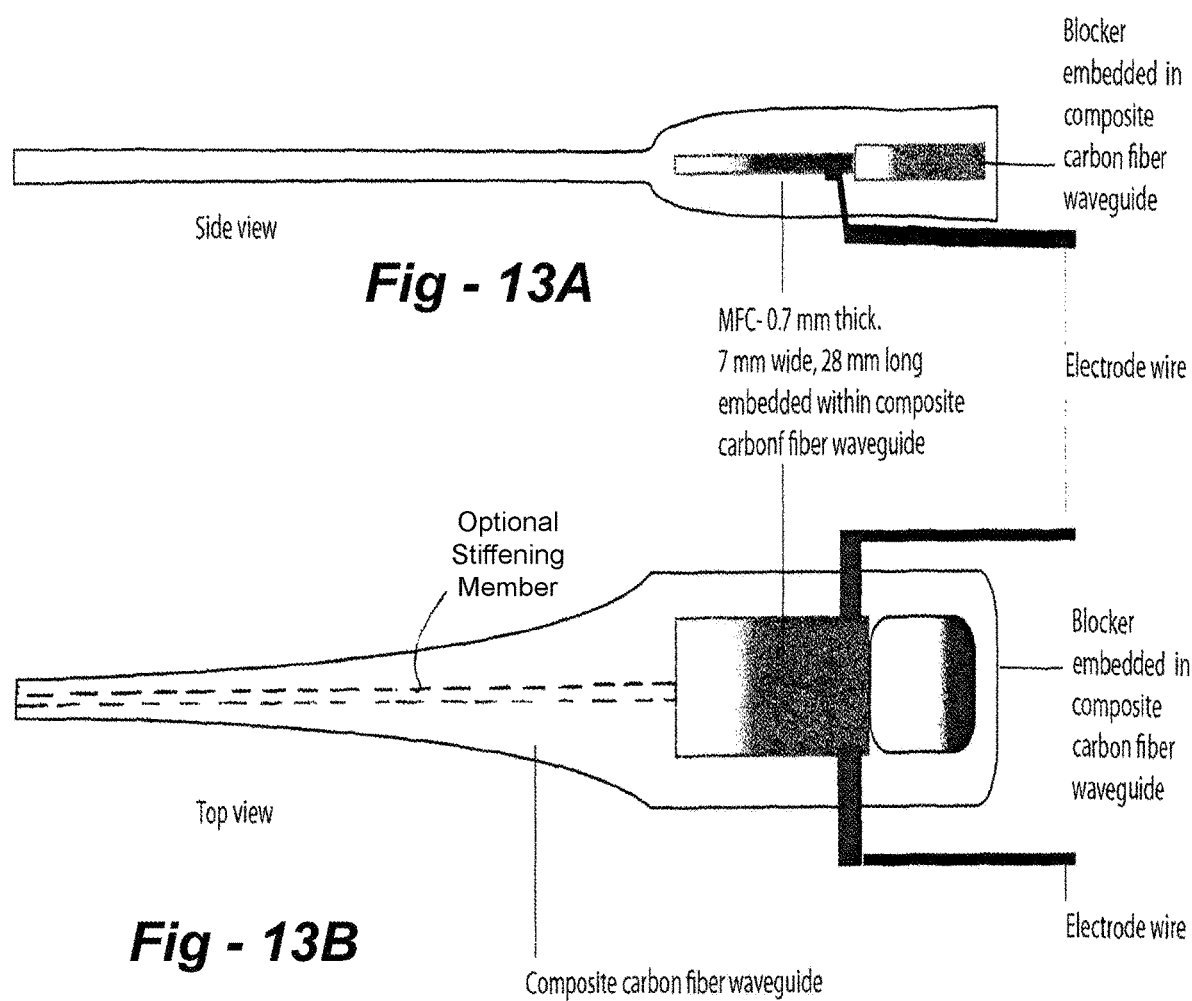
FIG. 13A is a side view of an MFC embedded in a carbon fiber waveguide.
FIG. 13B is a top view of the embodiment of FIG. 13A.

As the plies are laid up, the mold can be created to accommodate an embedded device like an MFC as shown in FIG. 13. FIG. 13A is a side view, and FIG. 13B is a top view. This has advantage in that of the six sides of the MFC, when applied to the probe surface only one side is transmitting sound energy to the probe. Embedded within the probe with all sides contributing energy to the probe the composite makes for more efficient transfer of energy. Thinness of the composite overlying the embedded MFCs leads to more efficient heat transfer. This also allows the presence of more MFCs on the surface for increase power or for causing bending/whipping action in the y mode. An embedded MFC creates a thinner more ergonomic device and allows an endoscope space to work in the nose. Note that the blocker may optionally be embedded within the material as well or, alternatively, mounted externally particularly if physical adjustment is desirable.

As typical carbon fiber materials are made with overlapping sheets and oriented filaments, the direction of the filaments may be important to accomplish purposes such as soft tissue crushing or cutting. It has been found that if the fibers are placed such that they line up in parallel and continuous form from proximal to distal, the result is a high modulus beam that efficiently transmits energy and movement, delivering it very effectively to the tip and target tissue. That is, with the fibers running in the longitudinal direction, parallel to each other and from proximal to distal, the fibers are capable of transmitting force in that plane with little if any buckling due to the high modulus and any incorporated change is shape e.g. a ridge along the flat surface or a cupped shape. For the purposes of this device as used on soft tissue this is very effective. If force applied through these fibers on very hard tissue such as bone leads to buckling, shape can be reinforced with a rib of carbon fiber or other stiff material to strengthen the planar surface. Also, if bone effects are not desirable the buckling can be left to occur by changes in thickness to a thinner material or different composite.

The layers within the composite may also be varied. Furthermore, a thin sheet of for example fiberglass may be used to enclose and isolate an electrical device from the carbon fiber. Special fabrics can be incorporated to add strength, change wave formation, change speed of sound, and/or provide for heat conduction/removal. Other fabrics for those knowledgeable in the art can be used such as graphene of which has a very high speed of sound so that the resonant frequency could be much higher than in previous materials and it conducts heat very efficiently. Embedded passive stiffening material can also be added.

As previously mentioned the x plane of a flat probe separates the motion of the z and y planes. While the x plane does not move it can passively carry an extension in that plane or even off plane. The z movement of the probe along the longitudinal axis carries, passively, the projection in the x plane and allows this projection to do work on the structures lateral to the probe.

Figure 18:
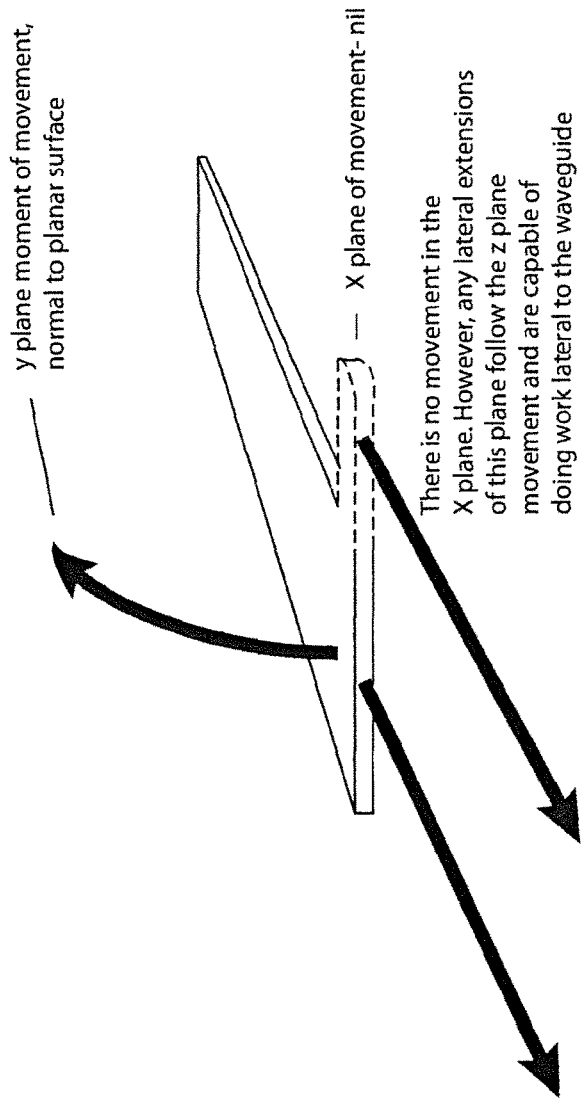
FIG. 18 illustrates tip movement.

FIG. 18 illustrates tip movement and shows the longitudinal (x) movement and normal movement (y) and, importantly also shows the lack of movement in the x plane. This Figure also shows an example of an extension in the x plane that moves passively as the z movement occurs. The extension can be at any angle though it is shown at 90 degrees here. With such an extension the device can reach areas not in line with the distal tip. As an example, to get into the sinuses that are lateral to the nasal passage this tip could reach laterally and be effective. In nasal surgery this could allow surgical action at the skull base, frontoethmoid region or into the maxillary sinus. Bending the probe may work but this way of getting to the sinuses and skull base, etc., is significantly different. Curves or bends in the waveguide probe can be linked to create shapes such as offset.

Figure 14:
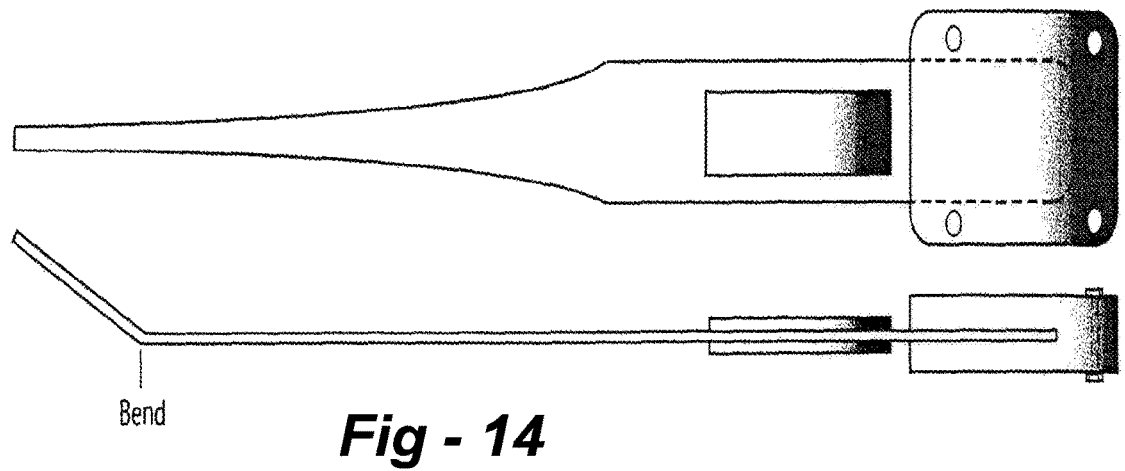
FIG. 14 is side view of a beam including an abrupt bend toward the distal end.

Due to the planar shape and to the speed of sound within the probe, as shown in FIG. 14, carbon fiber probes can be bent more acutely than metal and rod shaped probes. As the speed of sound increases the angle of bend can increase. As a rule of thumb the radius of curvature can decrease to roughly the length of a ¼ λ wave; however, the radius may be made smaller as the bend is placed closer to the distal end though there is some loss of energy. This allows the probe to deposit sound energy off the longitudinal axis and into the sides of the nasal cavity. Various surgical actions such as tissue disintegration and cutting can be applied to the sidewalls of the nasal passage and into the paranasal sinuses. Further, with the ability to enter a cavity, for example a paranasal sinus, ultrasonic action in clear liquids such as water, saline, antibiotics and/or antifungal agents can be activated to be effective against surface infections through cavitation, a therapeutic effect.

The Blocker

As with the Langevin design, the sound emanating in a proximal direction in the probe must be reflected. But unlike the Langevin design, there is no need for a very large blocking mass and condenser that wastes the proximally directed energy. Placed directly on the waveguide, the blocker can be effective because of its mass or its stiffness will cause at least some reflection of the sound back in a distal direction. In relation to the mass of the beam and the MFCs much smaller/less massive blocker material can be used. These can be attached mechanically or adhered with an adhesive such as epoxy. In this manner, sound waves are prevented from having a proximally directed action and sound can be reflect in a distal direction, and sound produced flows all to the distal end. Newton's third law comes into play here, and if the probe and tip assembly is very light, the blocker doesn't need to be very large and heavy to have a good ratio. As an example if the ratio of blocker to probe assembly mass is 20:1 only 5% of the proximal directed sound will be lost because of blocker motion.

Figure 15A:
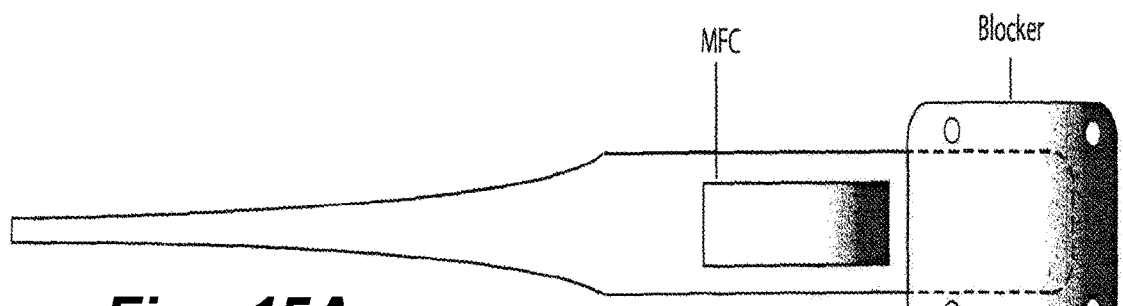
FIG. 15A is a side view of a waveguide with an adjustable blocking mass.
Figure 15B:
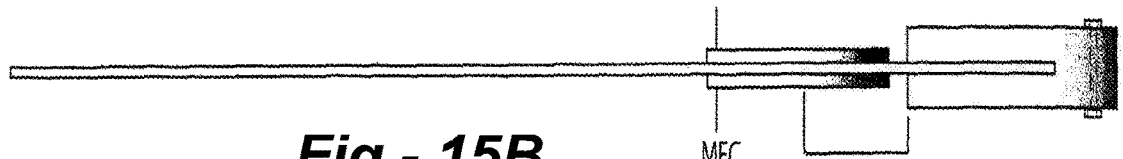
FIG. 15B is a top view of the embodiment of FIG. 15A.

Placement of the blocker is important in a resonant system. Since the block is on the waveguide itself, most of the sound will be reflected back to its origins in the MFC. The energy should arrive at the precise time to augment the next wave travelling distalward. Slightly early, or slightly late, and the reflected sound cancels the next wave. Once set this does not change. As seen in FIG. 15, by mounting the blocker onto the beam, the distance between the midpoint of the MFC and the distal edge of the blocker may be varied to optimize performance, including the favoring of resonant patterns for a different operational modes and applications. In addition, the blocking mass can have a channel cut into both sides such that the proximal end of the probe can sit within it, further helping reflect the sound as well as narrowing the proximal end as well a narrowing the region of the back blocker. This could also be made such that a narrowing of the probe near its proximal edge could engage a receiving edge of the blocker slot all to create an efficient reflection of energy and improved ergonomics. Because the mass of the MFCs is so small, the blocking mass does not have to be large as in the Langevin device. Weight is kept at a minimum, as is the overall size. A 1:20 ratio of MFC and probe to blocker mass is adequate.

Figure 19:
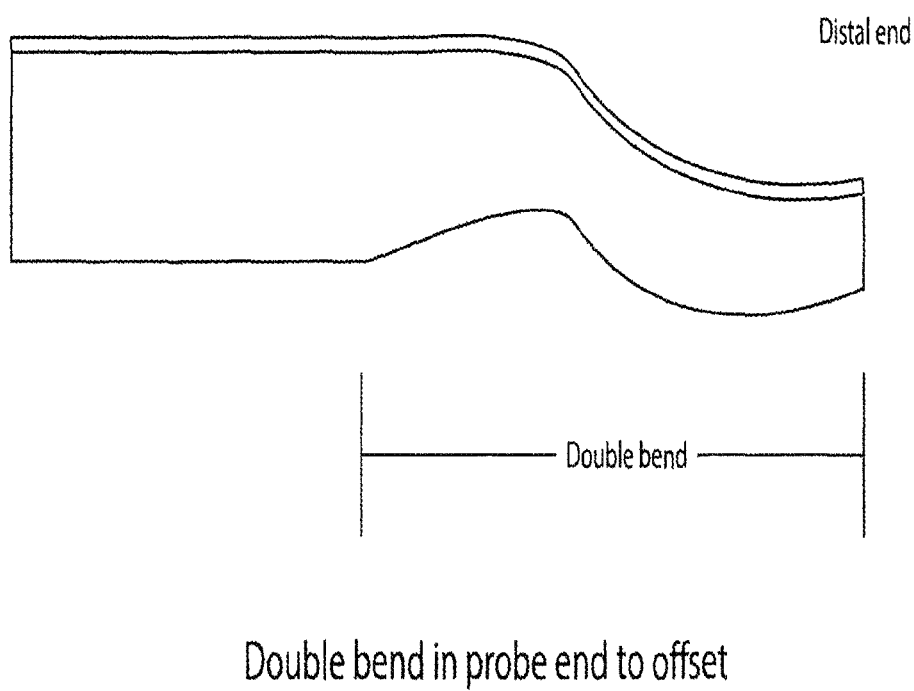
FIG. 19 illustrates a probe with a double bend.
Figure 20:
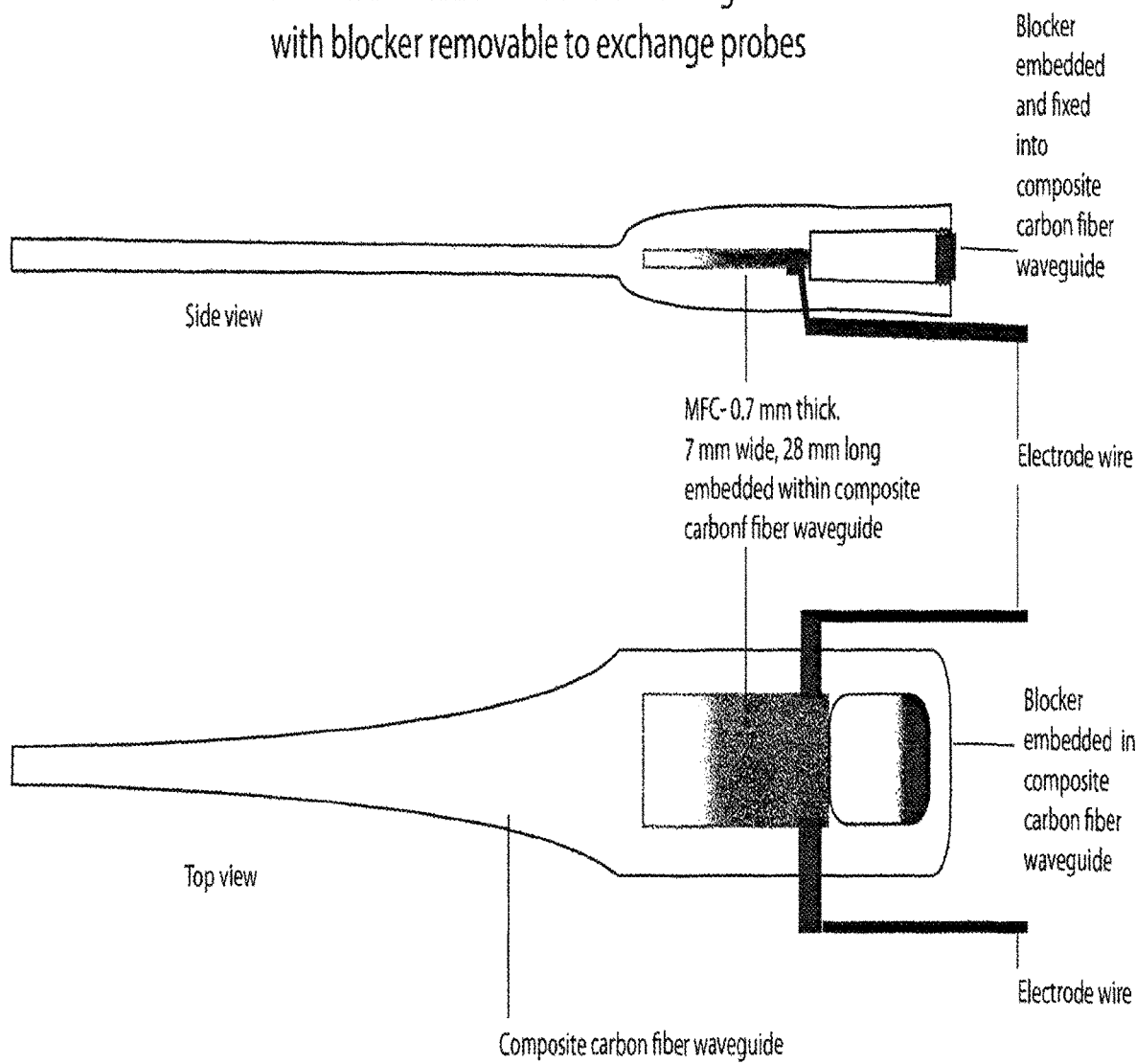
FIG. 20 depicts an embedded MFC and a removable blocker.
Figure 21:
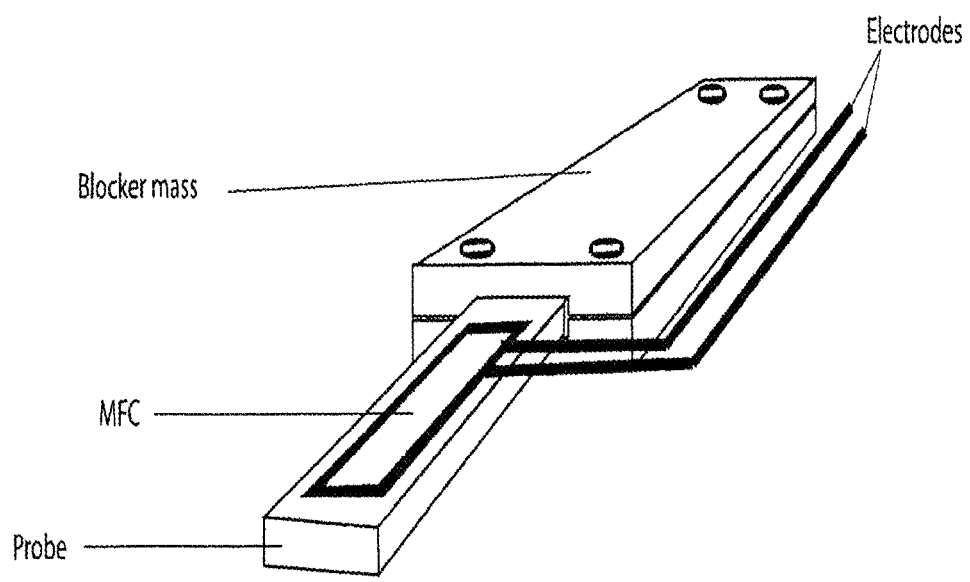
FIG. 21 illustrates a slotted blocker with a swappable probe.

FIGS. 19-21 illustrate different configurations applicable to the invention. In particular, FIG. 19 shows how the probe may include a series of bends in different directions. For example, two bends may be created in the probe to offset the position of the tip. The angles can be such that different effects can be created on the target tissue to cause dissecting, to disintegrating, to abrading, to penetrating, to elevating, to dissecting, to coagulating in any order needed or to apply ultrasonic energy for therapeutic effect as required by the disease situation. Multiple curves or bends in the distal end of probe may be provided to achieve activity lateral to probe such as in the paranasal sinuses that are found along the walls of the nasal passage.

FIG. 20 depicts an embedded MFC and a removable blocker, and FIG. 21 illustrates a slotted blocker with a swappable probe. While the descriptions of the probe assembly have all been with all parts fixed, it is possible to make some of the parts swappable and/or disposable, as shown in these Figures. For example the probe, carbon fiber or metal, may have the MFCs attached with leads extending from about the middle of the MFCs. The proximal end fits into a slot in the blocking mass with mechanical press fit and locking with for example cam clamps (not shown). This blocking mass/assembly can be opened and a probe with MFCs and a different tip attached for different application can be fitted into the slot. The blocking mass assembly is then tightened down on the proximal probe end. In this manner different probes for different purposes can be exchanged on the fly to from dissecting, to disintegrating, to abrading, to penetrating, to elevating, to dissecting, to coagulating in any order needed or to apply ultrasonic energy for therapeutic effect as required by the disease situation. Another preferred embodiment would be an embedded probe with the blocking mass slipping in and out of the posterior end and locking into place. Others familiar with the art will see other ways of swapping out probes with specific tips and specific constructions for specific purposes.

Tip Configurations

Figure 16:
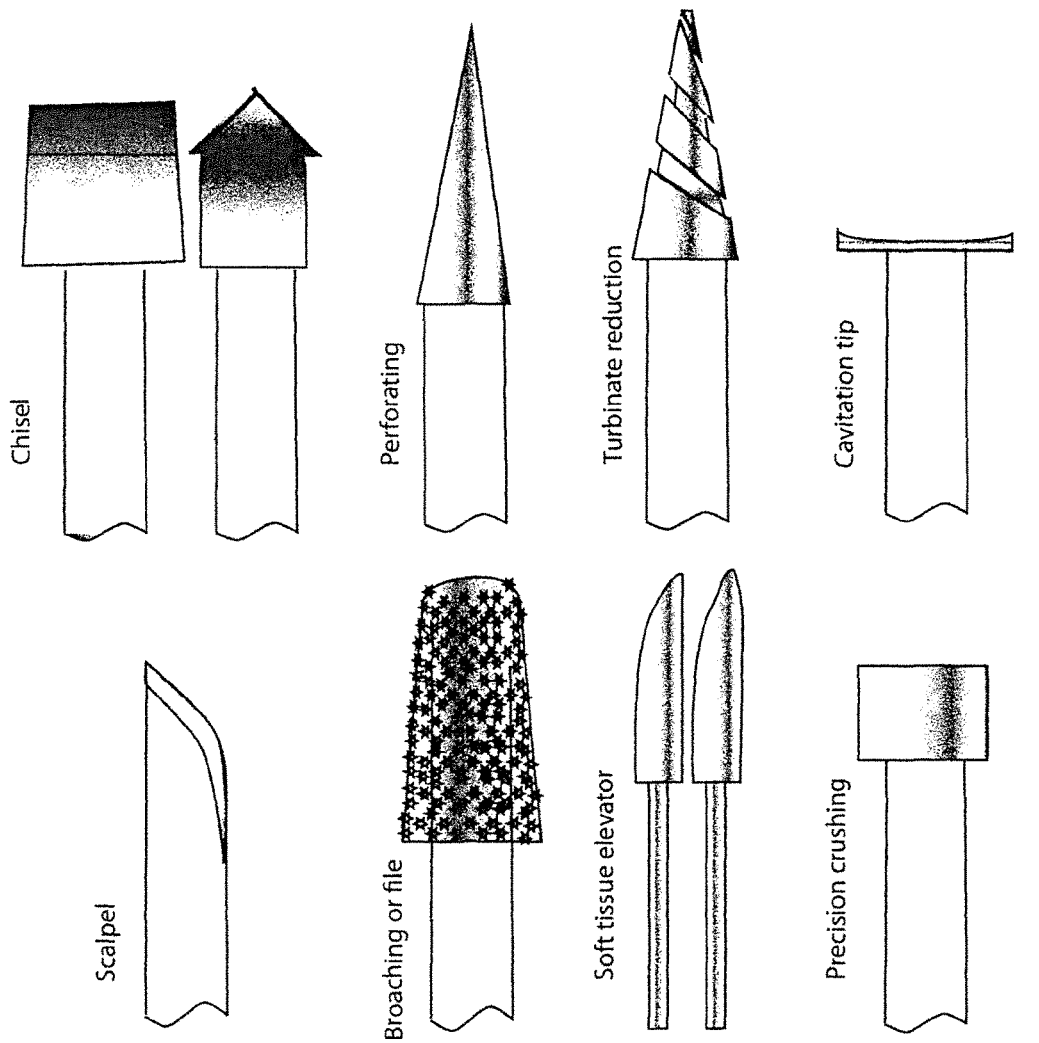
FIG. 16 illustrates various tip designs.

FIG. 16 illustrates various additional tip designs for different purposes. The following is a description of these basic designs. Those familiar with the art can expand on these or add other designs. These all can be added to the probe tip with appropriate adhesive. Mechanical means including through and through pins and layers of waveguide material on either side can secure the tip. The probe tip also can be fashioned without an added tip and further modified with shape and abrasive and coatings. The material used for these tips can be metals of various hardness, resins of many types and can have abrasive material embedded in the surface.

If tissue crushing is a predominant effect, the cross sectional area of the probe end holds significant importance for speed of tissue disintegration and removal of tissue. To this end, tips have been designed to augment the crushing effect.

The simplest tip is flat at the distal end and the material essentially wraps around the distal end of the probe thus increasing the cross-sectional area presented to the tissue. Add to that a sharp distal edge and there is obvious significant improvement. The tissue mulch that is produced needs to be removed from the front of the probe tip. Small troughs can be cut into the sides of the tip to allow for passive flow away from the active area and available for removal. As the probe moves in and out the recovery portion of the cycle can also be used to disintegrate. Thus with a flair to the proximal side of the tip and a sharp edge and again a trough to allow mulch to flow away, both aspects of the cycle are active. And again, as the probe is moving in and out the sides can be roughened to abrade or broach hard tissue such as bone, cartilage or dental surfaces. Small actions repeated at ultrasonic frequency can quickly achieve macro effects.

If the distal edge is curved like a scalpel blade and a reinforcing sharp metal edge is attached or a scalpel blade is attached this becomes a highly precise cutting tool. Chisel tips and abraiding tips can also be created for use on hard tissue like bone, cartilage or teeth. Pointed tips may be provided for piercing actions. Asymmetric tips, with one edge dull or sharpened, may be used use for elevating tissue for example the soft tissue coverings of the septum from the underlying cartilage or bone. Adding abrasives or file like ridges and the flat side can reduce or remove the bone or cartilage. A spiral shape ground into a pointed tip to increase surface area so when placed deep into tissue such as a turbinate it will cause destruction along the length of the tip. Combinations of these designs are possible.

A flat tip placed on angle to the probe end or a modification of the probe end can be made to be placed on a vessel where bleeding is occurring to produce movement that results in friction and thus heat to seal the leaking vascular structure.

A distal tip edge that flairs widely can cause cavitation on the negative stroke. The majority of the effect is just behind this flat tip end. This extends widely beyond the probe tip. If placed in a clear solution or solutions, possible with medication added this becomes a therapeutic device as the bacterial (planktonic or biofilm form) on the surface are destroyed directly.

It is seen from the descriptions of the engaging and active end of the probe that many modifications are possible for specific uses. Those familiar with the art will see many possibilities.

Enclosing Case Variations

The case that envelops the probe is a vital part of the system since it is used to carry and protect the probe, to accomplish cooling of the MFCs, carrying irrigation fluid and radiofrequency coagulation electrodes and suctioning away detritus from the tissue disintegration. In preferred embodiments, the case barely fits around the probe end and the shaft leaving a narrow passage between the probe and the inner surface of the case. It is open at the distal end from which the probe and tip projects. The distance between the inside of case and the probe is appropriate, at times narrow enough to produce a Bernoulli effect as tissue mulch is suctioned into the case. The case is electrically non conductive.

Figure 17:
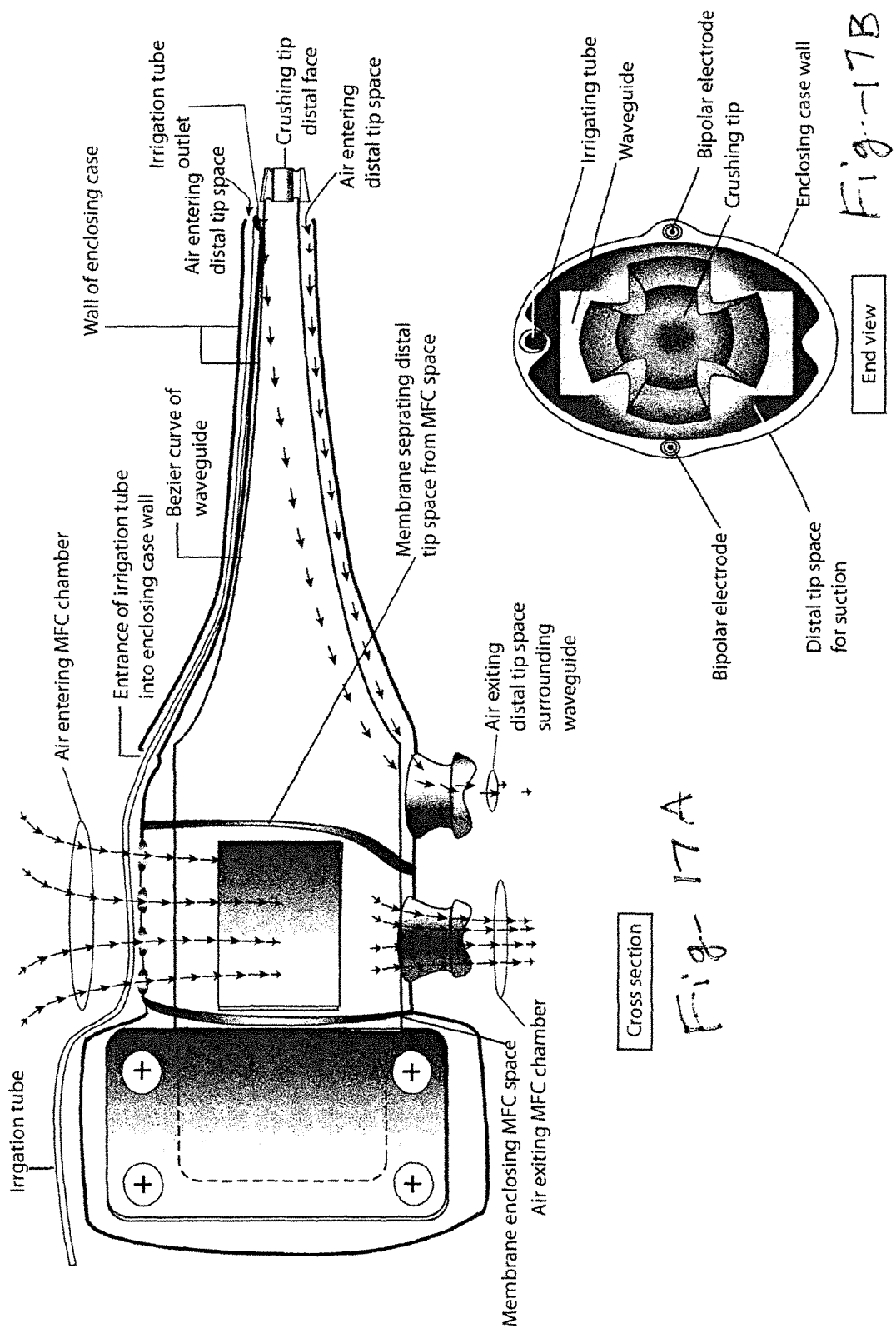
FIG. 17A is a cross section of an enclosure including the waveguide, MFC, blocker, irrigation, active tip, suction and cooling.
FIG. 17B is an end view of the instrument of FIG. 17A.

FIG. 17A is a cross section of an enclosure and FIG. 17B is an end view. These drawings are intended to show internal structures and are not to scale. Indeed, in preferred embodiments, the housing may be very slim, with the distal end being small enough to reach confined spaces in nasal cavities, as an example.

As shown in FIG. 17A, a thin tube is built into the case or it carries a fine hollow tube like a needle. This is used to drip a solution, either water, saline or therapeutic, onto the disintegration site. This both treats the area but also thins the mulch so that it can be moved through the case.

The case is built around the MFCs as well. In one preferred embodiment a flexible membrane may be bonded to the probe or MFC and extend to the inner surface of the case to form a water tight seal between the piezo region of the chamber and the distal dissection/disintegrating portion. This has been found to not dampen the action of the MFCs. Variously available suction devices are sufficient to keep the MFCs cool during even prolonged operation with even high voltages.

Cooling of the piezo/MFCs may be accomplished via air flow, taking the heat away with the air. In one preferred embodiment it has been found that the heat generated is low enough to be efficiently and effectively removed by air flow itself. Advantageously, this part of the case interior should be irregular or roughened or other more specific design like dimples to establish turbulent air flow that moves faster and carries heat away more efficiently than laminar flow. In one embodiment the air enters the MFC cavity passively or actively through a simple or complex opening in the superior surface of the device and evacuated by simple suction through a port attached to suction. Conversely, pressurized air can be pushed through the region. If desired water or other cooling can be employed. A manifold is used to collect the air sucked past the MFCs as well as handle detritus that has been evacuated from the action at the distal tip.

In one preferred embodiment, multiple suctioning actions may be provided, including one to remove tissue mulch and one to draw air across the MFCs for cooling. Two separate suction tubing, even with separate pumps, may be used, thus keeping the two systems separated, that is, the one for removing wet destroyed tissue and one for removing cooling air keeping electrical region separate from the liquid region. A manifold can be used to collect air from both the cooling chamber and the distal end. Those familiar with the art may want to combine the flows into one outflow tubing.

For hemostasis of larger vessels, electrodes can be placed within the side walls of the case. The electrodes may reside in a tube or cavity created within the case wall and loose enough that these electrodes can slide easily. In one preferred embodiment the electrodes may be constructed of a memory metal such that they will bend toward each other as they are pushed forward, free from the guide tube, to produce a bipolar electrocoagulation. Monopolar electrode could also be used. The generator produces RF frequency that coagulates blood. The distal suction clears the area.

The piezo electomechanical transducers are piezo crystals, usually lead zirconium titanate, that are evenly dispersed in a medium, either resin or ceramic. The resin has the advantage of bendability. The ceramic forfeits bendability for an increase in power for voltage applied. Such ceramic piezo material may achieve optimum tip movement at more than half the voltage. This allows reduced air flow cooling, as less heat needs to be removed, thereby providing a wide safety margin and longer piezo life time.

Where the case is held the surface can be coated with vibration reducing medium

The Generator

The generator is designed especially for this device with safety in mind. First, the generator is battery powered and is not grounded to earth for both patient and surgeon protection. This eliminates any possible harmful ground faults. Second, an embedded microprocessor is used to control all aspects of the generator including frequency setting adjustment, mode setting such as: Fz movement only, My movement only, Fz and My simultaneously, setting the power for the two modes independently measuring the voltages and currents being applied to the MFC devices as well as housekeeping activities as detailed below.

In addition, measuring the sensors that monitor the probe, and using that measurements to either maximize the distal end movement, or notify the surgeon of current viscosity and or bone detection.

The generator produces both triangular and square waves that are applied to the MFCs. A Half Bridge is used along with MOSFETS to produce high voltage square waves at a frequency determined by the microprocessor code. This may be used to power the My MFC or the Fz MFC's if desired. In this case, a triangular wave could be used to power the My MFC. This square wave is generated simultaneously with the triangle wave and their frequencies are totally independent. The square wave can also power the piezo MFC.

A sensor on the probe produces a voltage that is monitored by the generator. The generator can detect changes in voltage amplitude as different viscosities of tissue are encountered as well as being used for tuning the probe, the sensor will generate a signal that can be used to peak the resonance frequency causing maximum distal end movement. This can also be used to vary the power as needed at the same time this is relayed to the operator so that the viscosity change that represents the approach to bone can detected and adjust the power, and or adjust the instrument to either remove the bone, or stay away from it if it does not want to be destroyed. Thus, the operator/surgeon can be alerted to a change in viscosity, thereby indicating what the tip is encountering. For example, nearing a bony surface or breaking through to the air outside the target tissue.

A signal is produced that is the same frequency as the Fz signal, but has a continuous phase change of 360 degrees. This signal is the input to circuitry that drives a high luminosity LED that is positioned close to the distal end of the probe. This strobing of the LED will effectively slow down the distal end action so that it can be quantitatively measured using a microscope and a glass slide that has marks every 10 um or so. The complete phase change cycle can be adjusted so that the distal end appears to move in and out at a rate of 2 to 5 times a second. This is commonly known as the stroboscopic effect.

An emergency cutoff is built into the circuitry called an "ESTOP Switch". Pressing the switch disconnects the battery from the generator electronics and the probe power will stop in milliseconds.

A shaft encoder is implemented in a foot pedal. This encoder is read by the microprocessor and is used to adjust the power going to the MFC's. It may be implemented as a switch providing an on/off action, or be used as a linear actuator providing variable output power.

A USB port, or other connectivity device, connected to the microprocessor allows data gathering to a laptop or PC. It may also be used with a Bluetooth dongle to send wireless data to any Bluetooth enabled device. This port may send data that can be displayed on an oscilloscope. This will be the MFC Raw data generated by the triangle waveform or square wave normally connected to the Fz MFCs.

A Vacuum/Pressure variable voltage is generated. This voltage is connected to an H-Bridge for reversing the polarity of the voltage that is connected to a DC motor that drive a pump. The H-Bridge control signal determines if the pump is supplying a vacuum that can be used to evacuate tissue, or an air stream that can be used to un-clog the vacuum system, or be used to cool the MFC's. This feature can be especially valuable when AC power is not available for a conventional suction pump.

A variable DC power supply can be used to power a blower or small fan that can be used for cooling the MFC's. The Microprocessor monitors the MFC temperatures, so it can regulate the blower voltage to keep the MFC's within there working range, and yet not wasting valuable battery life.

There are provisions for connecting a MEMS microphone and monitoring it with the microprocessor. This microphone can be used as an alternative to using the sensor which is fastened on the probe. The microphone signal is converted to a DC level before it is connected to the microprocessor. This reduces the time the microprocessor must spend monitoring it.

The battery voltage is monitored and will prompt the user when it is time to charge it. A Polling Voltage is available to pole a new or used MFC. Further, this voltage is monitored by the Micro to detect correct poling operation, or a damaged or shorted MFC.

Having thus described our invention, we claim:

1. A probe adapted for insertion into a body passage so that it engages target tissues, comprising:
    a cantilevered beam having proximal and distal ends and a longitudinal axis;
    wherein the proximal end of the cantilevered beam is supported within a hand-held enclosure, and wherein the distal end of the cantilevered beam is operative to engage with target tissues;
    a blocking mass coupled to the proximal end of the cantilevered beam;
    an electromechanical transducer disposed on or within the beam between the blocking mass and the distal tip; and
    a microprocessor-controlled excitation system connected to electromechanical transducer, the excitation system being operative to apply reciprocating currents to the electromechanical transducer to control displaced motion of the distal end of the beam.

2. The probe of claim 1, wherein the microprocessor is programmable to vary the frequency of the reciprocating currents applied to the electromechanical transducer.

3. The probe of claim 1, wherein the microprocessor is programmable to generate extensional motion (Fz mode), characterized by a high-frequency, low displacement of the distal tip, and transverse motion (My mode), characterized by a low-frequency, large-displacement of the distal tip.

4. The probe of claim 3, wherein the microprocessor-controlled excitation system is operable to generate the Fz and My modes separately and in combination with one another.

5. The probe of claim 4, wherein the microprocessor-controlled excitation system further comprises a pulse width modulator (PWM) and a digital mode signal output to control relevant phases of the applied currents and generate the Fz and My modes.

6. The probe of claim 3, wherein the thickness of the beam is varied to emphasize the My or Fz movements.

7. The probe of claim 1, wherein the microprocessor-controlled electrical excitation system is powered only by a DC power supply.

8. The probe of claim 1, wherein the microprocessor-controlled electrical excitation system is programmable to provide sinusoidal, triangular, square or saw-tooth waveforms to the electromechanical transducer.

9. The probe of claim 1, including separate electromechanical transducer coupled to two opposed surfaces of the beam.

10. The probe of claim 1, including an electromechanical transducer embedded within the beam.

11. The probe of claim 1, including a beam composed of carbon fiber.

12. The probe of claim 11, including an electromechanical transducer embedded within the carbon-fiber beam.

13. The probe of claim 11, wherein at least some of the fibers of the carbon fiber beam are oriented in a proximal-to-distal direction.

14. The probe of claim 1, wherein the reciprocating currents applied to the electromechanical transducer result in a resonant energy pattern within the beam.

15. The probe of claim 1, wherein the position of the blocking mass is adjustable to control resonant energy pattern within the beam.

16. The probe of claim 1, wherein the blocking mass includes a slot or other structure to receive the proximal end of a removable/replaceable beam.

17. The probe of claim 1, further including a high-density polymer material to control the stiffness of the beam.

18. The probe of claim 1, further including:
    a sensor providing feedback to the microprocessor-controlled electrical excitation system regarding the density or viscosity of the tissues; and
    circuitry for (a) varying the output of the microprocessor-controlled electrical excitation system as a function of the sensed tissue density or viscosity, and (b) alerting the user regarding changes in the density or viscosity of the tissues.

19. The probe of claim 18, further including circuitry enabling sensor information to be recorded to a computer or other recording device.

20. The probe of claim 1, further including an independently controlled RF frequency signal to produce bipolar or monopolar electrocoagulation of tissue.

21. The probe of claim 1, further including separate electrodes to produce monopolar and bipolar RF electrocautery.

22. The probe of claim 21, including electrocautery electrodes composed of shape memory metal.

23. The probe of claim 1, wherein the enclosure facilitates air flow over the piezoelectric material for cooling purposes.

24. The probe of claim 1, further including an irrigation tube for delivering irrigation fluid to the distal tip.

25. The probe of claim 1, further including apparatus for suctioning removed tissues from the distal tip.

26. The probe of claim 1, further including interchangeable or fixed tips shaped to perform different crushing, cutting, abraiding, dissecting, heating of tissue, tissue removal, cavitation or combinations thereof.

27. The probe of claim 1, wherein the electromechanical transducer is piezoelectric.

28. The probe of claim 27, wherein the electromechanical transducer is a macro fiber composite (MFC).

29. The probe of claim 1, wherein the beam is substantially flat along its length.

30. The probe of claim 1, wherein the beam narrows from its proximal end to its distal end.

31. The probe of claim 30, including a transition from the proximal end of the beam to the narrower distal end thereof that is flat, curved or a combination thereof.

32. The probe of claim 1, wherein the cross section of the beam is cup-shaped.

33. The probe of claim 1, wherein the beam is solid or hollow.

34. The probe of claim 1, wherein the beam is laminated.

35. The probe of claim 1, wherein the beam is composed of resinous or monolithic material.

36. The probe of claim 1, wherein the probe is thinner or thicker to emphasize My or Fz movement.

37. The probe of claim 1, wherein the beam is bent at an angle away from the longitudinal axis.

38. The probe of claim 1, wherein the beam has projections configured to attack or interface with tissue.

39. The probe of claim 1, wherein the beam is constructed of composite fibrous material, and wherein at least some fibers are continuous along the longitudinal axis.

40. The probe of claim 1, wherein the beam or portions thereof are removably replaceable.

41. The probe of claim 1, wherein the beam includes ribs, cut outs, thinning or thickenings to modify the tip movement or tissue interaction.

42. The probe of claim 1, wherein the blocking mass is coupled to or embedded within the beam.

43. The probe of claim 1, further including a hand-held enclosure.

44. The probe of claim 43, wherein the enclosure is coated with vibration dampening material.

45. The probe of claim 43, wherein the enclosure separates the electomechanical transducer from the blocking mass, thus forming an internal chamber.

46. The probe of claim 43, wherein the enclosure includes a cavity with an air inlet that allows air to cool the electromechanical transducer.

47. The probe of claim 46, further including a pump for forcing the air over the electromechanical transducer.

48. The probe of claim 1, further including a plurality of electromechanical transducers.

49. The probe of claim 48, further including a generator operative to produce separate excitation currents to independently excite each electromechanical transducer.

50. The probe of claim 1, further including a generator operative to evaluate poling of the electromechanical transducer and repole as needed.

51. The probe of claim 1, wherein the blocking mass is made of metal, polymer or composite of appropriate modulus to absorb or reflect proximally directed sonic energy.

52. The probe of claim 1, wherein irrigation is applied using a separate removable cannula or entirely integrated into the case.

* * * * *